United States Patent [19]
Walsh et al.

[11] Patent Number: 5,743,477
[45] Date of Patent: Apr. 28, 1998

[54] INSECTICIDAL PROTEINS AND METHOD FOR PLANT PROTECTION

[75] Inventors: Terence A. Walsh, Zionsville, Ind.; Robert A. Houtchens, Milford, Mass.; James A. Strickland, Midland, Mich.; Gregory L. Orr, Ashley, Mich.; Donald J. Merlo, Midland, Mich.

[73] Assignee: DowElanco, Indianapolis, Ind.

[21] Appl. No.: 936,163

[22] Filed: Aug. 27, 1992

[51] Int. Cl.$^6$ .............................. A01N 63/00; C12N 9/20
[52] U.S. Cl. .............................. 424/94.6; 435/198
[58] Field of Search .................. 435/198; 424/94.6; 47/50, DIG. 11

[56] References Cited

U.S. PATENT DOCUMENTS

| | | | |
|---|---|---|---|
| 2,198,991 | 4/1940 | Dutton et al. | 117/3 |
| 4,797,276 | 1/1989 | Hermstadt | 424/84 |
| 4,940,840 | 7/1990 | Sunslow et al. | 424/84 |

FOREIGN PATENT DOCUMENTS

A-36568/89  12/1989  Australia.

OTHER PUBLICATIONS

Anthony H. C. Huang; "Lipases", *The Biochemistry of Plants*, vol. 9, pp. 91–119, 1987.

Robert A. Moreau, "Membrane-degrading enzymes in the tubers of various cultivars of solanum tuberosum", *J. Agric Food Chem.* 1985, 33, 36–39 (1985).

T. Galliard (1980), "Degradation of Acyl Lipids: Hydrolytic and oxidative enzymes", in The Biochemistry of Plants, vol. 4, ed. P. K. Stumpf, Academic Press, pp85–116.

R. Hofgen and Willmitzer (1990), Biochemical and genetic analysis of different patatin isoforms expressed in various organs of potato tuber protein, patatin. Nucleics Acids Res. 12:7987–8000.

D. L. Andrews, et al. (1988), Characterization of the lipid acyl hydrolase activity of the potato (*Solanum tubersum*) tuber protein, patatin, by cloning and abumdant expression in a baculovirus vector. Biochem. J. 252:199–206.

G.A. Mignery, et al., "Isolation and Sequece analysis of cDNAs for the major potato tuber protein, patatin" *Nucleic Acids Research*, vol. 12, No. 211, 7987–80012, 1984.

David A. Davis, William W. Currier and David Racusen, "Release of esterase from wounded potato tubers, etc.", *Can. J. Bot.* 67:1009–1013, Feb. 1988.

David Racusen and Murray Foote; "A Major soluble glycoprotein of potato tubers", *Journal of Food Biochemistry*, 4 (1980) 43–52.

Uwe Sonnewals, Arnde Sturm, etc. "Targeting and glycosylation of patatin the major potato tuber protein in leaves of transgenic tobacco", *Planta*(1989) 179:171–180.

S. Rosahl, J. Schell and L. Willmitzer, "Expression of a tuber-specific storage protein in transgenic tobacco plants". *The EMBO Journal*, vol. 6, No. 5, pp. 1155–1159, 1987.

David Racusen, "Lipid acyl hydrolase of papatin", *Can. J. Bot.* 62:1640–1644, Aug. 1983.

D.E. Foard et al., "Engineering of Crop Plants with Resistance to Herbivores and Pathogens: An Approach Using Primary Gene Products," *Plant Molecular Biology*, vol. 1, pp. 223–233, 1983.

Mark Vaeck et al., "Transgenic plants protected from insect attack," *Nature*, vol. 328, pp. 33–37, Jul. 1987.

X. Delannay et al., "Field Performance of Transgenic Tomato Plants Expressing the *Bacillus Thuringiensis* Var. Kurstaki Insect Control Protein," *Bio/Technology*, vol. 7, pp. 1265–1269, Dec. 1989.

S. Prat et al., "Gene expression during tuber development in potato plants," *Febs Letters*, vol. 268, No. 2, pp. 334–337, Aug. 1990.

Racusen Can. J. Bot. vol. 62 (8) 1640–1644 1984.

Primary Examiner—Rebecca E. Prouty
Attorney, Agent, or Firm—Donald R. Stuart

[57] ABSTRACT

The present invention provides a composition and method of using plant non-specific lipid acyl hydrolases to protect plants otherwise susceptible to insect infestation by one or more of corn rootworms, potato beetles, armyworms, borers, cutworms, wireworms, earworms and aphids.

5 Claims, 19 Drawing Sheets

Fig. 1A

```
  1    ATCTTTTTTA  ATTTTATTTT  TTATGATATT
 31    AGCAACTACT  AGTTCAACAT  GTGCTAAGTT
 61    GGAAGAAATG  GTGACTGTTC  TTAGTATTGA
 91    TGGAGGTGGA  ATTAAGGGAA  TCATTCCAGC
121    TACCATTCTC  GAATTTCTTG  AAGGACAACT
151    TCAGGAAGTG  GACAATAATA  AAGATGCAAG
181    ACTTGCAGAT  TACTTTGATG  TAATTGGAGG
211    AACAAGTACA  GGAGGTTTAT  TGACTGCTAT
241    GATAACTACT  CGAAATGAAA  ACAATCGACC
271    CTTTGCTGCT  GCCAAGATA   TTGTACCCTT
301    TTACTTCGAA  CATGGCCCTC  ATATTTTTAA
331    TTATAGTGGT  TCAATTATTG  GCCCAATGTA
361    TGATGGAAAA  TATCTTCTGC  AAGTTCTTCA
391    AGAAAAACTT  GGAGAAACTC  GTGTGCATCA
421    AGCTTTGACA  GAAGTTGCCA  TCTCAAGCTT
451    TGACATCAAA  ACAAATAAGC  CAGTAATATT
481    CACTAAGTCA  AATTTAGCAA  AGTCTCCAGA
511    ATTGGATGCT  AAGATGTATG  ACATATGCTA
541    TTCCACAGCA  GCAGCTCCAA  TATATTTTCC
571    TCCACATTAC  TTTATTACTC  ATACTAGTAA
601    TGGTGATATA  TATGAGTTCA  ATCTTGTTGA
```

Fig. 1B

```
 631   TGGTGGTGTT GCTACTGTTG GTGATCCGGC
 661   GTTATTATCC CTTAGCGTTG CAACGAGACT
 691   TGCACAAGAG GATCCAGCAT TTTCTTCAAT
 721   TAAGTCATTG GATTACAAGC AAATGTTGTT
 751   GCTCTCATTA GGCACTGGCA CTAATTCAGA
 781   GTTTGATAAA ACATATACAG CACAAGAGGC
 821   AGCTAAATGG GGTCCTCTAC GATGGATGTT
 851   AGCTATACAG CAAATGACTA ATGCAGCAAG
 881   TTCTTACATG ACTGATTATT ACATTTCTAC
 911   TGTTTTTCAA GCTCGTCATT CACAAAACAA
 941   TTACCTCAGG GTTCAAGAAA ATGCATTAAC
 971   ATGCATTAAC AGGCACAACT ACTGAAATGG
1001   ATGATGCGTC TGAGGCTAAT ATGGAATTAT
1031   TAGTACAAGT TGGTGAAAAA TTATTGAAGA
1061   AACCAGTTTC CAAAGACAGT CCTGAAACCT
1091   ATGAGGAAGC TCTAAAGAGG TTTGCAAAAT
1121   TGCTCTCTGA TAGAAAGAAA CTCCGAGCAA
1151   ACAAATCTTC TTATTAATTC AAGGTCTCGG
1181   GTTGTAGTAG TAACCTTACT ATGCTAAATA
1211   ATAAACGCTT GCAATATTTA TGATTGCACG
1241   CATTTAAGTA TTTCAACCTC AAAATAAAAA
```

Fig. 1C

```
1271  GGAGTTTGAG GGATAAATTT CAATAGAAAT
1301  GTCTCTCTAT GTAATGTGTG CTTGGATTAT
1331  GTAACCTTTT GGTTGTGTTA AATATTTAAA
1361  TAAATTATCG TTAAAAAAAA AAAAAAAAA
```

Fig. 2A

| | | | |
|---|---|---|---|
| 1 | CTAAATCTGT | TTTAGTTTTA | ATTTTTATGA |
| 31 | TATTAGCAAC | TACTAGTTCA | ACATTTGCTA |
| 61 | CGTTGGGAGA | AATGGTGACT | GTTCTTAGTA |
| 91 | TTGATGGAGG | TGGAATTAAG | GGAATCATTC |
| 121 | CGGGTATCAT | TCTCGAATTT | CTTGAAGGAC |
| 151 | AACTTCAGAA | AATGGACAAT | AATGCAGATG |
| 181 | CAAGACTTGC | AGATTACTTT | GATGTAATTG |
| 211 | GAGGAACAAG | TACAGGAGGT | TTATTGACTG |
| 241 | CTATGATAAC | TACTCCAAAT | GAAAACAATC |
| 271 | GACCCTTTGC | AGCTGCTAAA | GATATTGTAC |
| 301 | CTTTTTACTT | CCAACATGGC | CCTCATATTT |
| 331 | TTAATTCTAG | TACTGGCCAA | TTTTTTGGCC |
| 361 | CAAAATATGA | TGGAAAATAT | CTTATGCAAG |
| 391 | TGCTTCAAGA | AAAACTTGGA | GAAACTCGTG |
| 421 | TGCATCAAGC | TTTGACAGAA | GTTGCCATCT |
| 451 | CAAGCTTTGA | CATCAAAACA | AATAAGCCAG |
| 481 | TAATATTCAC | CAAGTCAAAT | TTAGCAAAGT |
| 511 | CTCCAGAATT | GGATGCTAAG | ATGTCTGACA |
| 541 | TATGTTATTC | CACAGCAGCA | GCTCCAACAT |
| 571 | ATTTCCCTCC | ACATTACTTT | GCTACTAATA |
| 601 | CTAGTAATGG | AGATAAATAT | GAGTTCAATC |

Fig. 2B

```
631   TTGTTGATGG  TGCTGTTGCT  ACTGTTGCTG
661   ATCCGGCGTT  ATTATCCGTT  AGCGTTGCAA
691   CGAGACGTGC  AGAAGAGGAT  CCAGCATTTG
721   CTTCAATTAG  GTCATTGAAT  TACAAGCAAC
751   TGTTGTTGCT  CTCATTAGGC  ACTGGCACTA
781   ATTCAGAGTT  TGATAAAACA  CATACAGCAC
811   AAGAGACAGC  TAAATGGGGT  GCTCTACAAT
841   GGATGTTGGT  TATACAGCAA  ATGACTGAGG
871   CAGCAAGTTC  TTACATGACT  GATTATTACC
901   TTTCTACTGT  TTTTCAAGAT  CTTCATTCAC
931   AAAACAATTA  CCTCAGGGTT  CAAGAAAATG
961   CATTAACAGG  CACAACTACT  AAAGCGGATG
991   ATGCTTCTGA  GGCTAATATG  GAATTATTAG
1021  TACAAGTTGG  TGAAAATTTA  TTGAAGAAAC
1051  CAGTTTCCAA  AGACAATCCT  GAAACCTATG
1081  AGGAAGCTCT  AAAGAGGTTT  GCAAAATTGC
1111  TTTCTGATAG  GAAGAAATTT  CGAGCAAACA
1141  AAGCATCTTA  TTAATTCAAG  GTCTCGGGTT
1171  GTAGTTGTAA  ATTTATTATG  CTAAATAATA
1201  AGCGCTTGCA  AAGTTCTATG  AGGGATAAAT
1231  TTCATTAGAA  ATGTCTCTCT  ATGTAATGTG
```

Fig. 2C

```
1261  TTGGATTATG  TAACCTTTTG  GTTGTGTTTA

1291  ATGTTTAAAT  AAATTATATA  TGGTGAAAAA

1311  AAAAAAAAAA  AAAAAAAA
```

Fig. 3A

```
                                               30
pDAB1008  .....SFLIL  FFMILATTSS  TCAKLEEMVT
            | |       ||||||||||  | |  ||||
pDAB1011  ....KSVLVL  IFMILATTSS  TFATLGEMVT 60
pDAB1008  VLSIDGGGIK  GIIPATILEF  LEGQLQEVDN
          ||||||||||  ||||  ||||  ||||||  ||
pDAB1011  VLSIDGGGIK  GIIPGIILEF  LEGQLQKMDN 90
pDAB1008  NKDARLADYF  DVIGGTSTGG  LLTAMITTRN
          | |||||||| ||||||||||  ||||||||| |
pDAB1011  NADARLADYF  DVIGGTSTGG  LLTAMITTPN 119
pDAB1008  ENNRPFAAAK  DIVPFYFEHG  PHIFNYS-GS
          ||||||||||  |||||||| |  ||||| | |
pDAB1011  ENNRPFAAAK  DIVPFYFQHG  PHIFNSSTGQ 149
pDAB1008  IIGPMYDGKY  LLQVLQEKLG  ETRVHQALTE
           ||  |||||  | ||||||||  ||||||||||
pDAB1011  FFGPKYDGKY  LMQVLQEKLG  ETRVHQALTE 179
pDAB1008  VAISSFDIKT  NKPVIFTKSN  LAKSPELDAK
          ||||||||||  ||||||||||  ||||||||||
pDAB1011  VAISSFDIKT  NKPVIFTKSN  LAKSPELDAK
```

Fig. 3B

```
                                                209
pDAB1008  MYDICYSTAA  APIYFPPHYF  ITHTSNGDIY
          | ||||||||  || |||||||  | |||||| |
pDAB1011  MSDICYSTAA  APTYFPPHYF  ATNTSNGDKY 239
pDAB1008  EFNLVDGGVA  TVGDPALLSL  SVATRLAQED
          ||||||| ||  || |||||||  ||||| | ||
pDAB1011  EFNLVDGAVA  TVADPALLSV  SVATRRAEED 269
pDAB1008  PAFSSIKSLD  YKQMLLLSLG  TGTNSEFDKT
          ||| || ||   ||| |||||||  ||||||||||
pDAB1011  PAFASIRSLN  YKQLLLLSLG  TGTNSEFDKT 299
pDAB1008  YTAQEAAKWG  PLRWMLAIQQ  MTNAASSYMT
          |||| ||||   |||| |||   || ||||||||
pDAB1011  HTAQETAKWG  ALQWMLVIQQ  MTEAASSYMT

329
B1008     DYYISTVFQA  RHSQNNYLRV  QENALTGTTT
          ||| |||||   ||||||||||  ||||||||||
pDAB1011  DYYLSTVFQD  LHSQNNYLRV  QENALTGTTT
```

Fig. 3C

```
                                                        359
pDAB1008  EMDDASEANM  ELLVQVGEKL  LKKPVSKDSP
          ||||||||||  |||||||||   ||||||||| |
pDAB1011  KADDASEANM  ELLVQVGENL  LKKPVSKDNP 386
pDAB1008  ETYEEALKRF  AKLLSDRKKL  RANKSSY*
          ||||||||||  ||||||||||  ||||  ||
pDAB1011  ETYEEALKRF  AKLLSDRKKF  RANKASY*
```

Fig. 10A

```
  1  AAGCTTGCAT GCCTGCAGAT CTGCATGGGT GGAGACTTTT CAACAAAGGG
 51  TAATATCCGG AAACCTCCTC GGATTCCATT GCCCAGCTAT CTGTCACTTT
101  ATTGTGAAGA TAGTGGAAAA GGAAGGTGGC TCCTACAAAT GCCATCATTG
151  CGATAAAGGA AAGGCCATCG TTGAAGATGC CTCTGCCGAC AGTGGTCCCA
201  AAGATGGACC CCCACCCACG AGGAGCATCG TGGAAAAAGA AGACGTTCCA
251  ACCACGTCTT CAAAGCAAGT GGATTGATGT GATCATCGAT GGAGACTTTT
301  CAACAAAGGG TAATATCCGG AAACCTCCTC GGATTCCATT GCCCAGCTAT
351  CTGTCACTTT ATTGTGAAGA TAGTGGAAAA GGAAGGTGGC TCCTACAAAT
401  GCCATCATTG CGATAAAGGA AAGGCCATCG TTGAAGATGC CTCTGCCGAC
451  AGTGGTCCCA AAGATGGACC CCCACCCACG AGGAGCATCG TGGAAAAAGA
501  AGACGTTCCA ACCACGTCTT CAAAGCAAGT GGATTGATGT GATATCTCCA
551  CTGACGTAAG GGATGACGCA CAATCCCACT ATCCTTCGCA AGACCCTTCC
601  TCTATATAAG GAAGTTCATT TCATTTGGAG AGAACACGGG GGACTCTAGA
651  GGATCCAGCT GAAGGCTCGA CAAGGCAGTC CACGGAGGAG CTGATATTTG
```

Fig. 10B

```
701   GTGGACAAGC TGTGGATAGG AGCAACCCTA TCCCTAATAT ACCAGCACCA
751   CCAAGTCAGG GCAATCCCCA GATCAAGTGC AAAGGTCCGC CTTGTTTCTC
801   CTCTGTCTCT TGATCTGACT AATCTTGGTT TATGATTCGT TGAGTAATTT
851   TGGGAAAAGC TCCTTTGCTG CTCCACACAT GTCCATTCGA ATTTACCGT
901   GTTTAGCAAG GGCGAAAAGT TTGCATCTTG ATGATTTAGC TTGACTATGC
951   GATTGCTTTC CTGGACCCGT GCAGCTGCGC TCGGATCTGG GGCCATTTGT
1001  TCCAGGCACG GGATAAGCAT TCAGCCATGG
``` ns in a new phenotype in the
INSECTICIDAL PROTEINS AND METHOD FOR PLANT PROTECTION The present invention relates to the fields of genetic engineering and plant husbandry. More specifically, the invention provides methods and compounds for controlling or combating insects in agriculture or horticulture.

Many vegetable and field crops are attacked by insect pests. For example, economically important phytophagous insects include corn rootworms e.g., Diabrotica spp., especially *D. barberi* (northern corn rootworm), *D. undecimpunctata* (cucumber beetles) and *D. virgifera* (western corn rootworm)); potato beetles (Leptinotarsa spp., especially *L. decemlineata*), armyworms (Spodoptera spp., especially *Spodoptera frugiperda*), borers (Ostrinia spp. and Diatraea spp., especially *Ostrinia nubilalis*), cutworms (especially Agrotisipsilon), wireworms (Elateridae, Agriotes spp.), earworms (Heliothis spp., especially *Heliothis zea*) and aphids (*Rhopalosiphum maydis* and *Schizaphis graminum*).

Control of such insects has traditionally been partially addressed by cultural and breeding methods. Most plants show some resistance to certain insects; the resistance can be physical or chemical. For example, the hairs on the leaves of many plants can stop small insects from getting near enough to the surface to chew it. In other cases plants use a range of complex secondary chemicals to make their tissues unattractive or toxic. An effective way to reduce these losses is to use crop cultivars having genes for pest resistance (see Painter (1951), *Insect Resistance in Crop Plants*, Macmillan: New York). Plant breeders have attempted to reduce losses caused by insect attack by incorporating insect resistance genes into their varieties via conventional breeding programs.

Classical approaches to host plant resistance, though remarkably successful in some instances, are rather empirical. Once "traits" for resistance are discovered, they are moved into agronomically acceptable lines by selection procedures. One limitation of the classical approach is that the movement of genes for resistance from one plant to another is restricted to species that can be interbred. Additionally, these types of resistance are likely to be under the control of many genes, and so are difficult for the plant breeder to fully exploit. Often resistant varieties have shown a yield depression and so have not been economically viable. Moreover, if no resistance can be identified within a species or within related species, then no improvement in insect pest resistance is possible by classical breeding.

Chemical insecticides have been heavily relied upon to control insects. These agents typically are applied on or banded into the soil, or to the plant foliage or in bait stations. In spite of the availability of a wide range of chemical pesticides, phytophagous insects remain a serious problem. Many chemical pesticides have the disadvantage of requiring repeated applications. A major problem in the use of many pesticides is the ability of insects to become resistant to the applied agents. This phenomenon occurs through selection of the most resistant members of the insect population during repeated application of the agent. A need, therefore, exists for new insect control agents, particularly agents that have a mode of action different from conventional insecticides.

As alternatives to synthetic compounds, certain naturally-occurring agents have been isolated and developed as pesticides. These include plant and microbial secondary metabolites and proteins, and natural predators or pathogens of insects (including other insects, fungi, bacteria and viruses). Furthermore, as recombinant DNA technology has advanced, genes from a donor organism may be transferred to a recipient organism resulting in a new phenotype in the recipient. In the case of transgenic plants, this phenotype may be resistant to insect damage if the introduced gene encodes a polypeptide, the action of which results in a deleterious effect on the pest. Consequently, there is a great interest and utility in finding polypeptides that have such an effect. Genes for these polypeptides can be used to modify organisms, especially plants and insect pathogens, so that they adversely affect the growth and development of insect pests. A very limited number of such polypeptides have been described, e.g., polypeptides from *Bacillus thuringiensis*, various proteinaceous protease and amylase inhibitors, various plant lectins, etc. However, to date no publication has suggested the use of plant non-specific lipid acyl hydrolases for use in insect control.

Plant non-specific lipid acyl hydrolases have been identified from a variety of plant sources including potato tubers, flowers and leaves, bean leaves and rice bran. The activity of plant non-specific lipid acyl hydrolases is extremely high in many tissues. Although their action in causing rancidity in stored agricultural products and in damaged or infected tissues has been quite well documented, their in vivo physiological role is still unclear.

Speculation on the role of lipid acyl hydrolases has mainly been centered on their involvement in the turnover of membrane lipids. Alterations of membrane lipids occur in development and differentiation, such as during seed maturation and germination and fruit ripening. In addition, the free fatty acids released from the enzymatic reaction may undergo oxidation catalyzed by several known oxidases to produce nonvolatile and volatile metabolites that may be of hormonal nature. In injured potato tuber cells, the hydrolytic and acyl-transferring activities of lipid acyl hydrolase, together with lipoxygenase, may release cytotoxic, oxidized fatty acid derivatives and water-insoluble waxes that inhibit microbial invasion.

An object of the present invention is to provide a method for protecting a plant or a part thereof from insect pests.

A further object of the present invention is to provide novel compositions which are capable of protecting from attack a plant or a part thereof otherwise susceptible to insect infestation by one or more of corn rootworms, potato beetles, armyworms, borers, cutworms, wireworms, earworms and aphids.

A further object of the present invention is to provide a process for preparing genetically transformed host cells comprising the transformation of host cells with a gene encoding a protein capable of having a deleterious effect, upon ingestion, by one or more of corn rootworms, potato beetles, armyworms, borers, cutworms, wireworms, earworms and aphids.

Other objects and advantages of the present invention will become apparent from the description of the invention provided hereunder.

Accordingly, in one aspect, the invention relates to a method of controlling one or more of corn rootworms, potato beetles, armyworms, borers, cutworms, wireworms, earworms and aphids. It is especially concerned with providing a plant non-specific lipid acyl hydrolase in, on or near a plant tissue otherwise susceptible to attack by one or more of such insects, whereby the plant tissue has improved resistance to such insects.

In a second aspect, the invention relates to transformed cells which possess genes encoding a plant non-specific lipid acyl hydrolase capable of protecting from attack a plant tissue otherwise susceptible to insect infestation by one or more of corn rootworms, potato beetles, armyworms, borers, cutworms, wireworms, earworms and aphids.

In a third aspect, the present invention relates to a method of preparing an insecticidal composition of at least one plant non-specific lipid acyl hydrolase, wherein the composition is capable of improving the resistance of plants or parts thereof susceptible to insect infestation by one or more of corn rootworms, potato beetles, armyworms, borers, cutworms, wireworms, earworms and aphids.

In other aspects, the invention is directed to expression vehicles capable of effecting the production of such aforementioned proteins in suitable host cells. It also includes the host cells and cell cultures which result from transformation with these expression vehicles.

A number of aspects of the present invention are further illustrated in the accompanying Drawings, in which:

FIGS. 1A–1C show the nucleotide sequence of a patatin cDNA insert (SEQ. ID. NO. 1) in pDAB1008. The end of the sequence coding for a first patatin isoform is underlined.

FIGS. 2A–2C show the nucleotide sequence of a patatin cDNA insert (SEQ. ID. NO. 2) in pDAB1011. The end of the sequence coding for a second patatin isoform is underlined.

FIGS. 3A–3C show polypeptide sequences of two patatin cDNAs (SEQ. ID. NO. 3 and 4, respectively). Amino acids are numbered from the initiator methionine of full-length prepatatin. Vertical bars indicate identity of sequence, and dashes indicate the absence of amino acids. The expected amino-termini of the mature patatins are underlined.

FIGS. 10A–10B show a nucleotide sequence of a promoter comprising the doubly-enhanced CaMV 35S promoter, and a deleted ADH1 sequence inserted into an MSV leader sequence.

Figure 4:
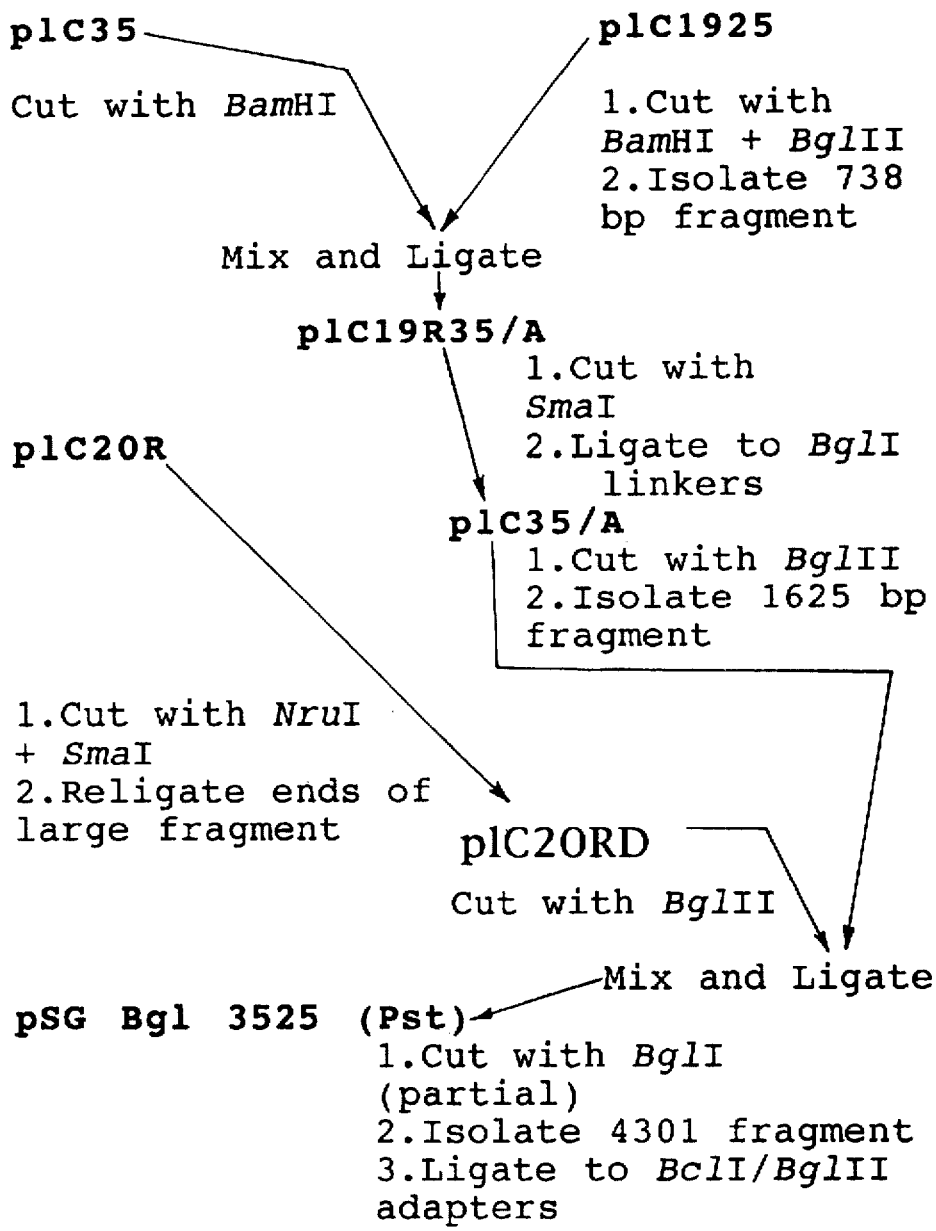
FIGS. 4, 5, 6, 7 and 8 show a flow diagram of the construction of pDAB219Δ.
Figure 5:
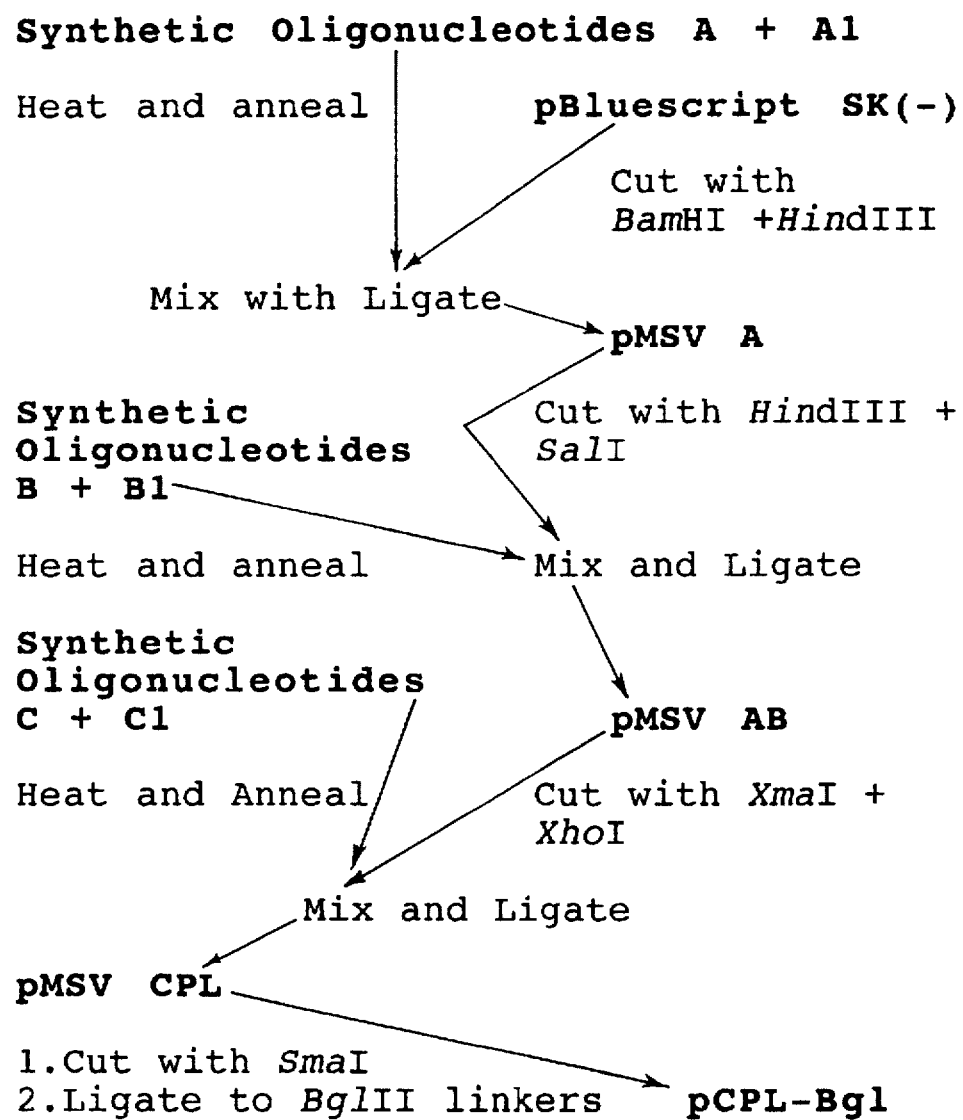
Figure 6:
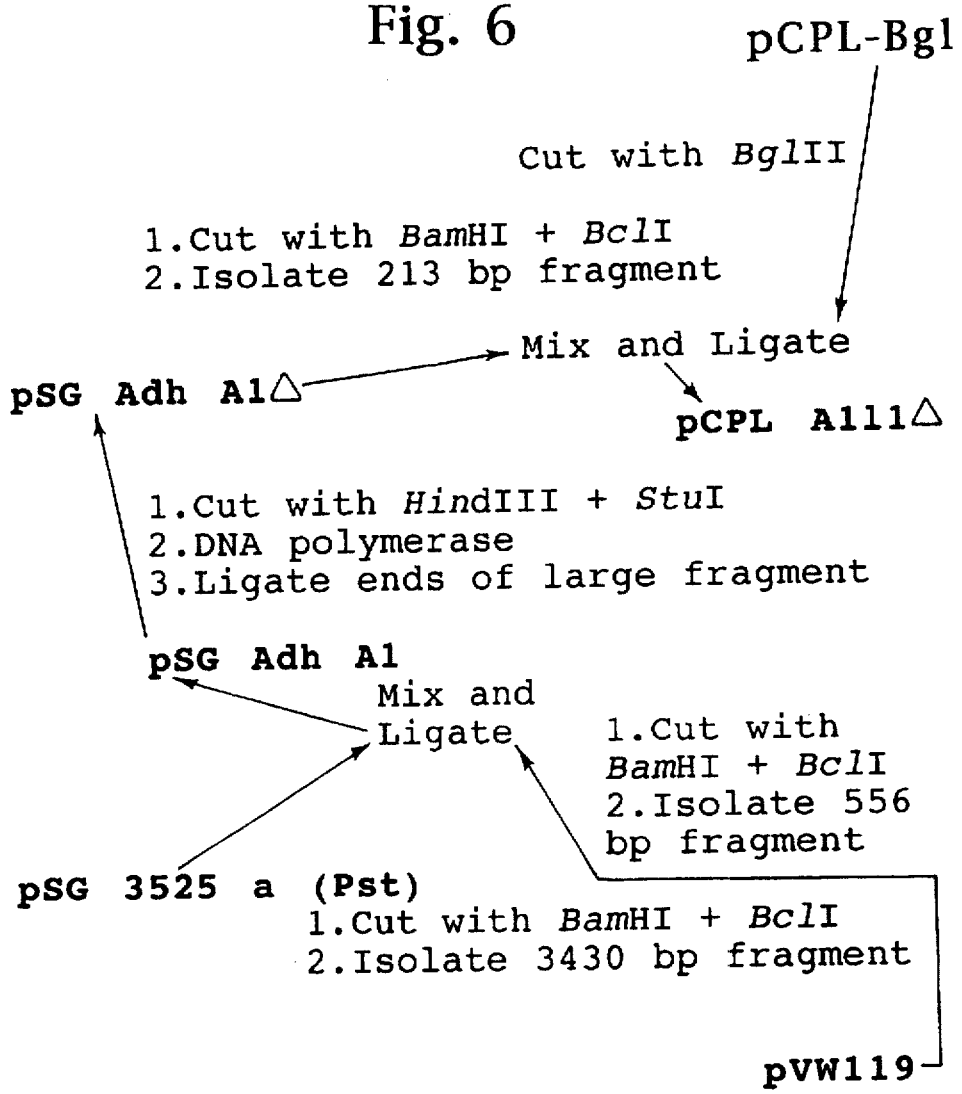
Figure 7:
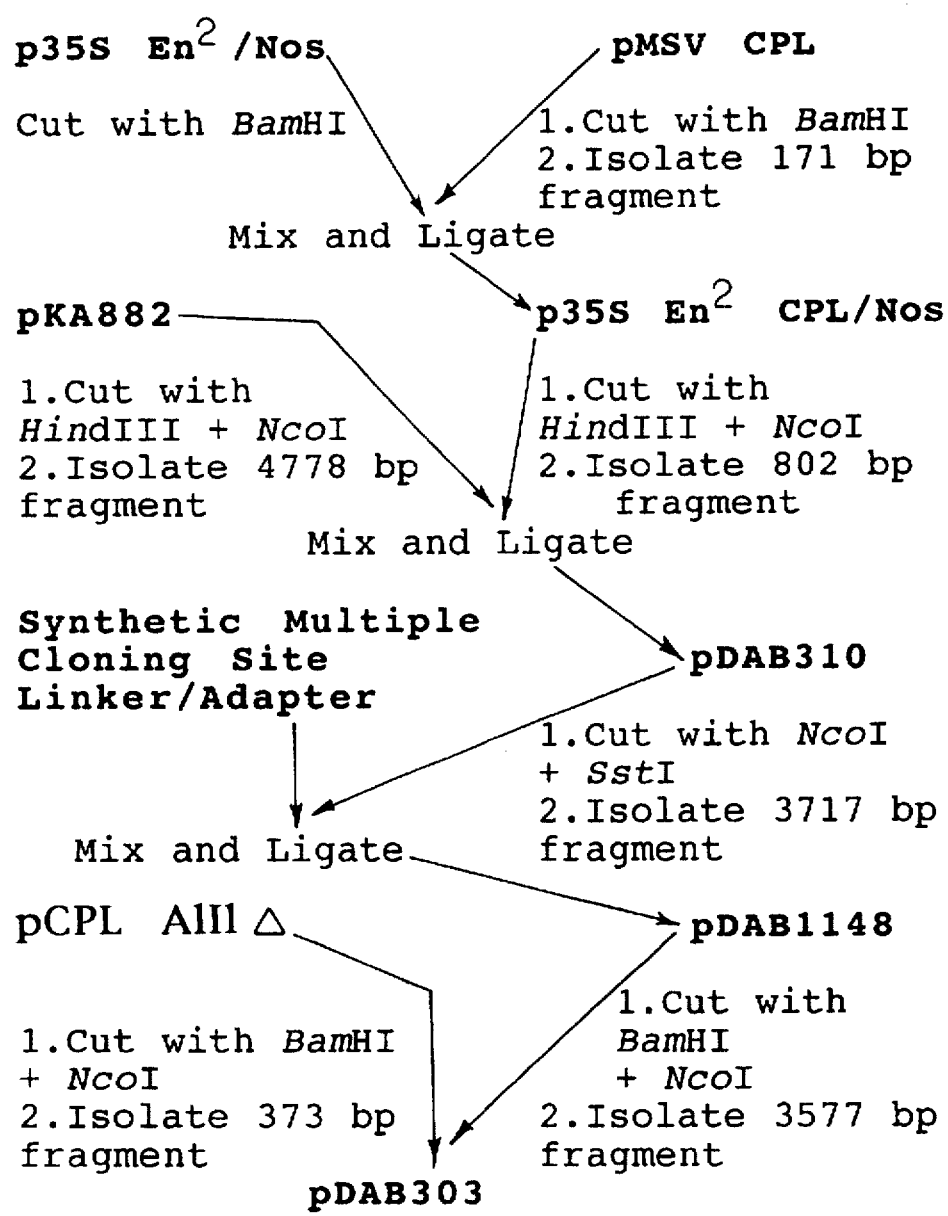
Figure 8:
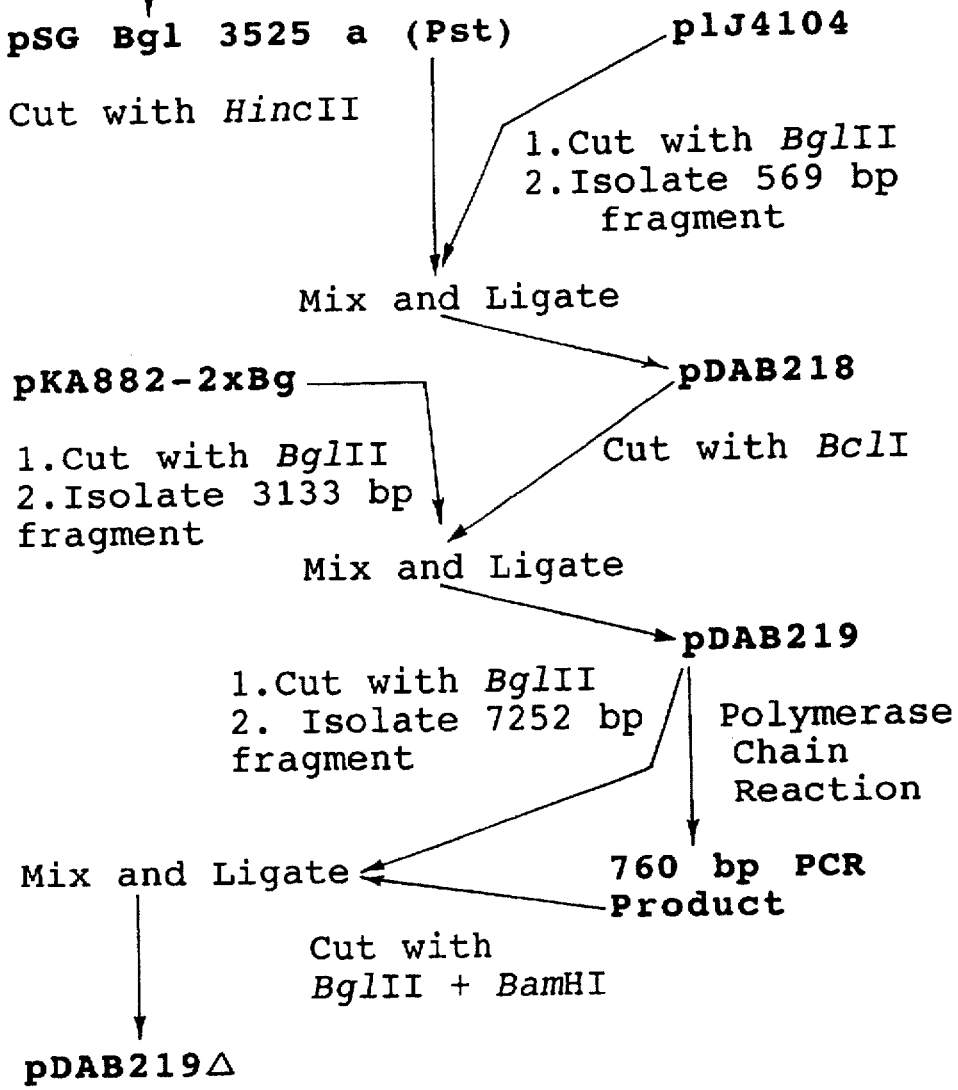

The entire teachings of all references cited herein are hereby incorporated by reference.

It has now been surprisingly found that plant non-specific lipid acyl hydrolases can control insect growth (including larvae) of one or more of corn rootworms, potato beetles, armyworms, borers, cutworms, wireworms, earworms and aphids.

An "insect controlling amount" is an amount of a plant non-specific lipid acyl hydrolase sufficient to deleteriously disrupt the normal life processes of an insect [i.e., amounts which are lethal (toxic) or sublethal (injuring, growth or development inhibiting or repelling)].

As used herein the term "plant non-specific lipid acyl hydrolase" includes a protein that hydrolyzes acyl groups from at least one of several classes of lipids, including glycolipids, phospholipids, sulfolipids, and mono- and diacylglycerols, but is inactive on triacylglycerols. The acyl hydrolase releases both fatty acids from diacyl glycerolipids, and in many cases, there is no preference for either the 1- or 2-position of the acyl ester linkage. Thus, the enzyme possesses a combined catalytic capacity of phospholipase A1, A2 and B, as well as glycolipase, sulfolipases and monoacylglycerol lipase. Similarities of the plant non-specific lipid acyl hydrolase enzymes from various tissues include the following: (1) they exert a similar pattern of substrate specificity as described above; (2) they may occur as isozymes in each tissue and they have fairly similar patterns of substrate specificity; (3) the activity ratio of the enzyme preparation on galactolipid and phospholipid remains fairly constant throughout an enzyme purification procedure; and (4) the enzyme carries out acyltransferase reactions with each of the substrates (Galliard, T. (1980). In: "The Biochemistry of Plants" (P. K. Stumpf and E. E. Conn eds.), Vol. 4, pp 85–116, Academic Press, New York).

The most studied plant non-specific lipid acyl hydrolase is patatin, the most abundant protein in the storage parenchyma cells of potato tubers (*Solanum tuberosum* L.) (see Racusen and Foote (1980), *Journal of Food Biochemistry*, 4:43–52). Patatin is a mixture of at least 6 to 10 closely-related polypeptides, or isoforms, which differ in their primary sequence, patterns of glycosylation, and hydrolytic activities (Hofgen and Willmitzer (1990), *Plant Science*, 66:221–230). They are encoded by a family of about 15 genes per haploid genome (Twell & Ooms (1988), *Mol. Gen. Genet.*, 212:325–336). The genes encoding several patatin isoforms have been sequenced and published (see Mignery et al. ((1984), *Nucleic Acids Research*, 12:7987–8000). Further, the sequences of genes encoding additional patatin isoforms are set forth in FIGS. 1 and 2.

Patatin is synthesized as an approximately 43,000 kilodalton (43 kDa) preprotein with a 23 amino-acid amino-terminal signal peptide. After passage through the endoplasmic reticulum and Golgi complex (where the polypeptide is glycosylated) the protein is targeted to the vacuole where it accumulates as a mature protein of about 40 kDa during tuber development. However, the patatin-like polypeptide found in flowers appears to be approximately 3 kD larger than the mature patatin obtained from tubers (Vancanneyt, et al. (1989), *Plant Cell*, 1:533:540).

The present invention specifically contemplates the use of any of the patatin isoforms. There are slight differences in the various isozymes; however, the homology between the isoforms of patatin has been demonstrated by amino-terminal amino acid sequence analysis and comparison of characterized genomic and CDNA sequences. In fact, it is generally known that variations may exist in the amino acid sequence of a protein without any significant effect on its functional characteristics.

Plant non-specific lipid acyl hydrolases are present in other plant tissues as well. Those skilled in the art recognize that such other plant non-specific lipid acyl hydrolases exhibiting insect control of corn rootworms, potato beetles, armyworms, borers, cutworms, wireworms, earworms and aphids are included within the scope of present invention.

Leaf enzymes from *Phaseolus mutlifora* (see Burns et al. (1977), *Biochem Soc. Trans*, 5:1302–1304), *P. vulgaris* (see Matsuda and Hirayama (1979), *Biochim. Biophys. Acta*, 573:155–165) and potato (see Matsuda et al. (1980), *Agric. Biol. Chem.*, 43:563–570) exhibit a pattern of substrate specificity similar to patatin. Furthermore, patatin and the leaf enzymes generally have an optimal activity at acidic pH.

The enzyme from rice bran can release fatty acids from different lysophospholipids, with the highest activity on lysophosphatidylcholine containing palmitic acid (see Matsuda and Hirayama (1979), *Agric. Biol. Chem.*, 43:463–469).

Several forms of a lysophospholipase have been purified from barley endosperm in postgermination. The enzyme is a polypeptide with a molecular mass of 36 kDa and an extra mass of 10 to 12 percent (see Fujikura and Baisted (1985), *Arch. Biochem. Biophys.*, 234:570–578). Hydrolase activity that releases fatty acids from phosphatidylcholine and lysophosphatidylcholine is present in barley grains (see von Rebmann and Acker (1973), *Fette. Seifen Anstrichm.*, 75:409–411. A plant non-specific lipid acyl hydrolase that releases fatty acid from sulfolipids has been detected in alfalfa leaves and roots, and in maize roots (see Yagi and Benson (1962), *Biochim. Biophys. Acta*, 57:601–603).

A patatin-like protein has been described from sweet pepper (Vancanneyt (1989), supra). Additionally, activities have been noted in eggplant leaf and fruit, pumpkin, pepper, radish, barley, carrot, tomato, soybean, tobacco, beet, pea and spinach (Moreaun (1987), *Phytochem.,* 26:1899–1902).

Using a biochemical assay that monitors the esterolytic or lipolytic activity of a plant non-specific lipid acyl hydrolase, a skilled artisan may routinely survey plants for proteins with plant non-specific lipid acyl hydrolase activity. Generally, protease activity may be measured essentially using any one of a variety of known assay procedures (see Wolfson and Murdock (1987), supra), and Andrews et al. (1988), (*Biochem. J.,* 252:199–206). To validate that the presence of the plant non-specific lipid acyl hydrolase in the diet of the target insect would indeed suppress the growth of its populations, a second screen may be applied in which the purified or partially purified plant non-specific lipid acyl hydrolase is added on or into the laboratory diet, or applied to the plant surface.

Once appropriate activity is determined, the amino acid sequence of the plant non-specific lipid acyl hydrolase, or at least a portion thereof, may be determined by N-terminal sequencing or sequencing of oligopeptides derived by proteolysis. In addition, antisera can be prepared that specifically recognizes the plant non-specific lipid acyl hydrolase.

It should be understood that, given the present teachings, one may synthesize or isolate substantially pure functional derivatives of the naturally-occurring plant non-specific lipid acyl hydrolases. A "functional derivative" of the plant non-specific lipid acyl hydrolase is a compound which possesses a biological activity that is substantially similar to a biological activity of the plant non-specific lipid acyl hydrolase. The term functional derivative is intended to include "fragments", "effectively homologous variants", or "analogues".

A "fragment" is meant to refer to any hydrolytically-active polypeptide subset of a plant non-specific lipid acyl hydrolase molecule.

An "effectively homologous variant" of a molecule such as the plant non-specific lipid acyl hydrolase is meant to refer to a molecule substantially similar in sequence and function to either the entire molecule or to a fragment thereof. For purposes of this invention, one amino acid sequence is effectively homologous to a second amino acid sequence if at least 70 percent, preferably at least 80 percent, and most preferably at least 90 percent of the active portions of the amino acid sequence are identical or equivalent. General categories of potentially-equivalent amino acids are set forth below, wherein, amino acids within a group may be substituted for other amino acids in that group: (1) glutamic acid and aspartic acid; (2) lysine, arginine and histidine; (3) alanine, valine, leucine and isoleucine; (4) asparagine and glutamine; (5) threonine and serine; (6) phenylalanine, tyrosine and tryptophan; and (7) glycine and alanine. More importantly and critical to the definition, the function of a second amino acid sequence is effectively homologous to another amino acid sequence if the second amino acid sequence conforms to a tertiary structure having the capacity to hydrolyze acyl groups from a lipid substrate.

An "analog" of a molecule such as the plant non-specific lipid acyl hydrolase is meant to refer to a molecule substantially similar in function to either the entire molecule or a fragment thereof. Thus, provided that two molecules possess a similar activity, they are considered analogs as that term is used herein even if the structure of one of the molecules is not found in the other, or if the sequence of amino acid residues is not identical.

As used herein, the term "substantially pure" is meant to describe the plant non-specific lipid acyl hydrolase which is homogeneous by one or more purity or homogeneity characteristics. For example, a substantially pure plant non-specific lipid acyl hydrolase will show constant and reproducible characteristics within standard experimental deviations for parameters such as molecular weight, chromatographic behavior and the like. The term, however, is not meant to exclude artificial or synthetic mixtures of the plant non-specific lipid acyl hydrolase with other compounds. The term is also not meant to exclude the presence of minor impurities which do not interfere with the biological activity of the plant non-specific lipid acyl hydrolase and which may be present, for example, due to incomplete purification.

A substantially pure plant non-specific lipid acyl hydrolase may be purified directly from plants in which they are naturally occurring by any appropriate protein purification technique. Exemplary techniques include chromatographic techniques, such as gel filtration liquid chromatography, ion exchange chromatography, high performance liquid chromatography, reverse phase chromatography or by the use of immunological reagents employing plant non-specific lipid acyl hydrolase-specific antibodies.

It is possible to synthesize invitro a plant non-specific lipid acyl hydrolase from the constituent amino acids (see Merrifield (1963), *J. Amer. Chem. Soc.,* 85:2149–2154; and *Solid Phase Peptide Synthesis* (1969), (eds.) Stewart and Young). The peptides thus prepared may be isolated and purified by procedures well known in the art (see *Current Protocols in Molecular Biology* (1989), (eds.) Ausebel, et al., and Sambrook et al. (1989), *Molecular Cloning: A Laboratory Manual*).

Although it is possible to determine and synthesize the entire amino acid sequence of the plant non-specific lipid acyl hydrolase, it is preferable to isolate the entire sequence of the plant non-specific lipid acyl hydrolase gene. DNA encoding a plant non-specific lipid acyl hydrolase may be prepared from chromosomal DNA, cDNA or DNA of synthetic origin by using well-known techniques.

Genomic DNA encoding plant non-specific lipid acyl hydrolase may be isolated by standard techniques (Sambrook et al. (1989), supra). Specifically comprehended as part of this invention are genomic DNA sequences encoding allelic variant forms of the plant non-specific lipid acyl hydrolase gene, as well as its 5' and 3' flanking regions. It is also possible to use primers and exponentially amplify DNA invitro using sequence specified oligonucleotides by the polymerase chain reaction (PCR) (see Mullis et al. (1987), *Meth. Enz.,* 155:335–350; Horton et al. (1989), *Gene,* 77:61; and *PCR Technology: Principles and Applications for DNA Amplification,* (ed.) Erlich (1989).

A DNA isolate encoding a plant non-specific lipid acyl hydrolase may also be obtained from a complementary DNA (cDNA) library. cDNA preparations are ligated into suitable recombinant vectors to form a gene library. Alternatively, the cDNAs may be expressed in a vector such as λgt11 and the library screened using antibodies against the plant non-specific lipid acyl hydrolase.

A suitable oligonucleotide or set of oligonucleotides may be used, by techniques well known in the art, to screen the genomic DNA or CDNA libraries. To facilitate the detection of the desired sequence, the oligonucleotide probe may be labeled with any material having a detectable physical or chemical property. General procedures for isolating, purifying and sequencing the desired sequences are well known in the art (see *Current Protocols in Molecular Biology* (1989), supra; and Sambrook et al. (1989), supra).

An alternative method of obtaining a genetic sequence which is capable of encoding the plant non-specific lipid acyl hydrolase is to prepare it by oligonucleotide synthesis, after the gene sequence of interest is determined (see Caruthers (1983), In: *Methodology of DNA and RNA*, (ed.) Weissman; or Beaucage et al.(1981), (*Tetrahedron Letters*, 22:1859–1962). A series of oligonucleotides may be synthesized in order to provide a series of overlapping fragments which when annealed and ligated will produce both strands of the gene. These fragments are then annealed and ligated together using well-known techniques (see Sambrook et al. (1982), supra). Alternatively, the gene may be produced by synthesizing a primer having a so-called "wagging tail", that does not hybridize with the target DNA; thereafter, the genomic sequences are amplified and spliced together by overlap extension (see Horton et al. (1989), *Gene*, 77:61–68). The resulting DNA fragment with the predicted size is isolated by electrophoresis and ligated into a suitable cloning vector for amplification and further manipulation (see Mullis et al. ( 1987), supra; and *PCR Technology: Principles and Applications for DNA Amplification*, supra).

Of course, one may incorporate modifications into the isolated sequences including the addition, deletion, or non-conservative substitution of a limited number of various nucleotides or the conservative substitution of many nucleotides, provided that the proper reading frame is maintained. Translational stop and start signals are added at the appropriate points, and sequences to create convenient cloning sites are added to the ends. Exemplary techniques for modifying oligonucleotide sequences include using polynucleotide-mediated, site-directed mutagenesis (see Zoller et al. (1984), *DNA*, 3:479–488; Higuchi et al. (1988), *Nucl. Acids Res.*, 16:7351–7367; Ho et al. (1989), *Gene*, 77:51–59; and Horton et al. (1989), *Gene*, 77:61; and *PCR Technology: Principles and Applications for DNA Amplification*, (ed.) Erlich (1989)).

In order to further characterize such genetic sequences, it is desirable to introduce the sequence into a suitable host to express the proteins which these sequences encode, and confirm that they possess characteristics of plant non-specific lipid acyl hydrolases. Techniques for such manipulations are well known in the art and disclosed by Sambrook et al. (1989), supra.

Vectors are available or can be readily prepared for transformation of viruses, prokaryotic or eukaryotic cells. In general, plasmid or viral vectors should contain all the DNA control sequences necessary for both maintenance and expression of a heterologous DNA sequence in a given host. Such control sequences generally include a promoter sequence having, a transcriptional start, a leader sequence, a DNA sequence coding for translation start-signal codon, a translation terminator codon, and a DNA sequence coding for a 3' non-translated region containing signals controlling termination of RNA synthesis and/or messenger RNA modification. Finally, the vectors should desirably have a marker gene that is capable of providing a phenotypical property which allows for identification of host cells containing the vector, and an intron in the 5' untranslated region, e.g., intron 1 from the maize alcohol dehydrogenase gene that enhances the steady state levels of mRNA.

Exemplary host cells include prokaryotic and eukaryotic strains. The appropriate procedure to transform a selected host cell may be chosen in accordance with the host cell used. Based on the experience to date, there appears to be little difference in the expression of genes, once inserted into cells, attributable to the method of transformation itself.

Conventional technologies for introducing biological material into host cells include electroporation [see Shigekawa and Dower (1988), *Biotechniques*, 6:742; Miller, et al. (1988), *Proc. Natl. Acad. Sci. USA*, 85:856–860; and Powell, et al (1988), *Appl. Environ. Microbiol.*, 54:655–660]; direct DNA uptake mechanisms [see Mandel and Higa (1972), *J. Mol. Biol.*, 53:159–162; Dityatkin, et al. (1972), *Biochimica et Biophysica Acta*, 281:319–323; Wigler, et al. (1979), *Cell*, 16:77; and Uchimiya, et al. (1982), In: *Proc. 5th Intl. Cong. Plant Tissue and Cell Culture*, A. Fujiwara (ed.), Jap. Assoc. for Plant Tissue Culture, Tokyo, pp. 507–508]; fusion mechanisms [see Uchidaz, et al. (1980), In: *Introduction of Macromolecules Into Viable Mammalian Cells*, C. Baserga, G. Crose, and G. Rovera (eds.) Wistar Symposium Series, Vol. 1, A. R. Liss Inc., NY, pp. 169–185]; infectious agents [see Fraley, et al. (1986), *CRC Crit. Rev. Plant Sci.*, 4:1–46; and Anderson (1984), *Science*, 226:401–409]; microinjection mechanisms [see Crossway, et al. (1986), *Mol. Gen. Genet.*, 202:179–185]; and high velocity projectile mechanisms (see EPO 0 405 696).

The appropriate procedure to transform a selected host cell may be chosen in accordance with the host cell used. Based on the experience to date, there appears to be little difference in the expression of genes, once inserted into cells, attributable to the method of transformation itself.

Transformants are isolated in accordance with conventional methods, usually employing a selection technique, which allows for selection of the desired organism as against unmodified organisms. Generally, after being transformed, the host cells are grown for about 48 hours to allow for expression of marker genes. The cells are then placed in selective and/or screenable media, where untransformed cells are distinguished from transformed cells, either by death or a biochemical property. The selected cells can be screened for expression of the plant non-specific lipid acyl hydrolase by assay techniques such as immunoblot analysis, enzyme-linked immunosorbent assay, radioimmunoassay, or fluorescence-activated cell sorter analysis, immunohistochemistry and the like. The transformed tissues are then tested for insect-controlling activity.

A host cell may be transformed to provide a source from which significant quantities of the vector containing the gene of interest can be isolated for subsequent introduction into the desired host cells or for which significant quantities of the protein may be expressed and isolated. Exemplary recombinant host cells include unicellular prokaryotic and eukaryotic strains. Prokaryotic microbes that may be used as hosts include *Escherichia coli*, and other Enterobacteriaceae, Bacilli, and various Pseudomonas. Common eukaryotic microbes include *Sacchromyces cerevisiae* and *Pichia pastoris*. Common higher eukaryotic host cells include Sp2/0 or CHO cells. Another preferred host is insect cells, for example Drosophila larvae, in which the vector contains the Drosophila alcohol dehydrogenase promoter. Alternatively, baculovirus vectors, e.g., *Autographa californica* nuclear polyhedrosis virus (see Miller et al. (1983), *Science*, 219:715–721) may be engineered to express large amounts of the plant non-specific lipid acyl hydrolase in cultured insects cells (see Andrews et al. (1988), *Biochem. J.*, 252:199–206).

The present invention provides an agricultural composition for application to plants or parts thereof which are susceptible to infestation by one or more of corn rootworms, potato beetles, armyworms, borers, cutworms, wireworms, earworms and aphids, said agricultural composition comprising one or more plant non-specific lipid acyl hydrolase.

Often the agricultural composition will contain an agriculturally acceptable carrier. By the term "agriculturally acceptable carrier" is meant a substance which may be used to dissolve, disperse or diffuse an active compound in the composition without impairing the effectiveness of the compound and which by itself has no detrimental effect on the soil, equipment, crops or agronomic environment.

The agricultural compositions may be applied in a wide variety of forms including powders, crystals, suspensions, dusts, pellets, granules, encapsulations, microencapsulations, aerosols, solutions, gels or other dispersions. In addition to appropriate liquid or solid carriers, compositions may include adjuvants, such as emulsifying and wetting agents, spreading agents, dispersing agents, adhesives or agents which stimulate insect feeding according to conventional agricultural practices. Adjuvants for the formulation of insecticides are well known to those skilled in the art.

The concentration of plant non-specific lipid acyl hydrolase will vary widely depending upon the nature of the particular formulation, particularly whether it is a concentrate or it is to be used directly. The plant non-specific lipid acyl hydrolase will be present in at least 1 percent by weight and may be up to 100 percent by weight.

The presentation of the agricultural composition may be achieved by external application either directly or in the vicinity of the plants or plant parts. The agricultural compositions may be applied to the environment of the insect pest(s), e.g., plants, soil or water, by spraying, dusting, sprinkling, or the like.

The present invention further contemplates using recombinant hosts (e.g., microbial hosts and insect viruses) transformed with a gene encoding the plant non-specific lipid acyl hydrolase and applied on or near a selected plant or plant part susceptible to attack by a target insect. The hosts may be capable of colonizing a plant tissue susceptible to insect infestation or of being applied as dead or non-viable cells containing the plant non-specific lipid acyl hydrolase. Microbial hosts of particular interest will be the prokaryotes and the lower eukaryotes, such as fungi.

Characteristics of microbial hosts for encapsulating a plant non-specific lipid acyl hydrolase include protective qualities for the protein, such as thick cell walls, pigmentation, and intracellular packaging or formation of inclusion bodies; leaf affinity; lack of mammalian toxicity; attractiveness to pests for ingestion; ease of killing and fixing without damage to the plant non-specific lipid acyl hydrolase; and the ability to be treated to prolong the activity of the plant non-specific lipid acyl hydrolase. Characteristics of microbial hosts for colonizing a plant include non-phytotoxicity; ease of introducing a genetic sequence encoding a plant non-specific lipid acyl hydrolase, availability of expression systems, efficiency of expression and stability of the insecticide in the host.

Illustrative prokaryotes, both Gram-negative and -positive, include Enterobacteriaceae, such as Escherichia; Bacillaceae; Rhizoboceae, such as Rhizobium and Rhizobacter; Spirillaceae (such as photobacterium), Zymomonas, Serratia, Aeromonas, Vibrio, Desulfovibrio, Spirillum; Lactobacillaceae; Pseudomonadaceae (such as Pseudomonas and Acetobacter); Azotobacteraceae and Nitrobacteraceae. Among eukaryotes are fungi (such as Phycomycetes and Ascomycetes), which includes yeast (such as Saccharomyces and Schizosaccharomyces); and Basidiomycetes yeast (such as Rhodotorula, Aureobasidium, Sporobolomyces) and the like.

The present invention also contemplates the use of a baculovirus containing a gene encoding a plant non-specific lipid acyl hydrolase. Baculoviruses including those that infect *Heliothis virescens* (cotton bollworm), *Orgyla pseudotsugata* (Douglas fir tussock moth), *Lymantria dispar* (gypsy moth), *Autographica californica* (alfalfa looper), *Neodiprion sertifer* (European pine fly) and *Laspeyresia pomonella* (coddling moth) have been registered and used as pesticides (see U.S. Pat. No. 4,745,051 and EP 175 852).

The recombinant host may be formulated in a variety of ways. It may be employed in wettable powders, granules or dusts, or by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other insecticidal additives surfactants, and bacterial nutrients or other agents to enhance growth or stabilize bacterial cells. Liquid formulations may be aqueous-based or non-aqueous and employed as foams, gels, suspensions, emulsifiable concentrates, or the like. The ingredients may include rheological agents, surfactants, emulsifiers, dispersants, or polymers. In general, inoculants can be applied at any time during plant growth. Inoculation of large fields can be accomplished most effectively by spraying.

Alternatively, the plant non-specific lipid acyl hydrolase can be incorporated into the tissues of a susceptible plant so that in the course of infesting the plant the insect consumes insect-controlling amounts of the selected plant non-specific lipid acyl hydrolase. One method of doing this is to incorporate the plant non-specific lipid acyl hydrolase in a non-phytotoxic vehicle which is adapted for systemic administration to the susceptible plants. However, since the genes which code for plant non-specific lipid acyl hydrolase may be isolated, the invention contemplates, in a preferred embodiment, transgenic plants which are capable of biologically synthesizing plant non-specific lipid acyl hydrolase to provide the plants with a new, or an additional, mechanism of protection against attack by insects.

The invention provides methods of imparting resistance to insect infestation by one or more of corn rootworms, potato beetles, armyworms, borers, cutworms, wireworms, earworms and aphids to plants of a susceptible taxon, comprising: (a) culturing cells or tissues from at least one plant from the taxon; (b) introducing into the cells of the cell or tissue culture a structural gene encoding a plant non-specific lipid acyl hydrolase, operably linked to plant regulatory sequences which cause expression of the plant non-specific lipid acyl hydrolase gene in the cells, and (c) regenerating insect-resistant whole plants from the cell or tissues culture.

Obviously, the expression of uniquely high quantities of plant non-specific lipid acyl hydrolases may be deleterious to the plant itself. The use of a signal sequence to secrete or sequester in a selected organelle allows the protein to be in a metabolically inert location until released in the gut environment of an insect pathogen. Moreover, some proteins are accumulated to higher levels in transgenic plants when they are secreted from the cells, rather than stored in the cytosol (Hiatt, et al. (1989), *Nature*, 342:76–78).

The DNA sequence will generally be one which originates from, or has substantial sequence homology to a plant non-specific lipid acyl hydrolase, originating from a plant of a species different from that of the target organism. However, when the DNA sequence is one which originates from, or has substantial sequence homology to a plant non-specific lipid acyl hydrolase originating from, a plant of the same species as that of the target plant, such sequence may be expressed in significantly greater amounts.

In order to optimize the transcriptional and translational efficiency of such systems, it is possible to examine the frequency of codon usage and determine which codons are, in essence, preferred within the transcriptional and translational systems normally present in that plant. Using such preferred usage codons, it is possible to construct a protein coding sequence which may result in a significantly enhanced level of transcriptional and translational efficiency of the plant non-specific lipid acyl hydrolase gene compared to what would be achieved by taking the coding sequence directly in an unmodified form from the donor plant.

Generally, the insertion of heterologous genes appears to be random using any transformation technique; however, technology currently exists for producing plants with site specific recombination of DNA into plant cells (see WO/9109957). The activity of the foreign gene inserted into plant cells is dependent upon the expression characteristics of the individual inserted genes, resulting from control regions (promoters, polyadenylation regions, enhancers, etc.) and from the influence of endogenous plant DNA adjacent the chimeric insert and by the copy number.

The promoter selected should be capable of causing sufficient expression to result in the production of an insect controlling amount of protein. Suitable promoters may include both those which are derived from a gene which is naturally expressed in plants and synthetic promoter sequences which may include redundant or heterologous enhancer sequences. In cases where the sequence is derived from a plant source, one can use the 5' and 3' non-translated region naturally associated with the particular gene. A number of promoters which are active in plant cells include the nopaline synthase, octopine synthase and mannopine synthase promoters from the tumor-inducing plasmids of *Agrobacterium tumefaciens.*

In species which produce a plant non-specific lipid acyl hydrolase but in lower than insecticidal amounts, it may be preferable to overexpress the plant non-specific lipid acyl hydrolase in the same plant, and even tissue, from which it was derived, wherein the plant non-specific lipid acyl hydrolase is expressed at significantly greater levels than normally found. By significantly greater levels is meant the production of the plant non-specific lipid acyl hydrolase at levels at least 50% greater than normally found in untransformed plants of the same species. Accordingly, the present invention contemplates constitutive promoters such that the transformed plant has increased tolerance to insect pests. Examples of constitutive promoters include the CaMV 19S and 35S promoters (JP 63287485), ubiquitin promoter and the rice actin promoter (WO 9109948).

In species which produce a native plant non-specific lipid acyl hydrolase which is not produced in or not distributed to tissues which are normally infested with the insects, a tissue specific promoter can be used to provide localized expression of or overproduction of the plant non-specific lipid acyl hydrolase. Examples of tissue specific promoters include the root specific promoters such as maize met allothionein (EP 452269), the root specific promoter (WO/9113992) the plant seed storage body promoter (9113993), and the alcohol dehydrogenase-1 promoter. Promoters known to be light inducible include the promoter of the gene encoding the small subunit (ss) of the ribulose-1,5,-bisphosphate carboxylase from soybean and the promoter of the gene encoding the chlorophyll a/b binding protein in greening leaves (Coruzzi et al., (1983), *J. Biol. Chem.*, 258:1399; and Dunsmuir, et al. (1983), *J. Molecular and App. Gen.*, 2:285).

Finally, a wound or pathogen inducible promoter can be used to provide expression of the plant non-specific lipid acyl hydrolase when a tissue is attacked by a plant pest. Examples of wound or pathogen inducible promoters include the proteinase inhibitor II promoter.

Suitable vectors for transforming plant tissue and protoplasts have been described in the literature and are set forth herein (see deFrammond et al. (1983), *Biotechnology*, 1:262; An et al. (1985), *EMBO J.* 4:277; Potrykus et al. (1985), *Mol. Gen. Genet.* 199:183; Rothstein et al. (1987), *Gene*, 53:153; WO 90/08829 and WO 84/02913; and, in a preferred embodiment, pDAB219Δ and pDAB303 (as described in the Examples). It is not necessary in practice that the vector harboring the selectable marker gene also contains the gene of interest. Rather, co-transformation of such vectors may be used to transform plant cells.

The appropriate procedure to produce mature transgenic plants may be chosen in accordance with the plant species used. Regeneration varies from species to species of plants. Efficient regeneration will depend upon the medium, on the genotype and on the history of the culture. Once whole plants have been obtained, they can be sexually or clonally reproduced in such a manner that at least one copy of the sequence is present in the cells of the progeny of the reproduction. Such procedures may be chosen in accordance with the plant species used.

Mature plants, grown from the transformed plant cells, may be selfed to produce an inbred plant. In diploid plants, typically one parent may be transformed and the other parent may be the wild type. The parent will be crossed to form first generation hybrids ($F_1$), which are selfed to produce second generation hybrids ($F_2$). $F_2$ hybrids with the genetic makeup of plant non-specific lipid acyl hydrolase/plant non-specific lipid acyl hydrolase are chosen and selfed to produce inbred plants.

Conventional plant breeding methods can be used to transfer the plant non-specific lipid acyl hydrolase structural gene via crossing and backcrossing. Such methods comprise the further steps of (a) sexually crossing the insect-resistant plant with a plant from the insect-susceptible variety; (b) recovering reproductive material from the progeny of the cross; and (c) growing insect-resistant plants from the reproductive material. Where desirable or necessary, the agronomic characteristics of the susceptible variety can be substantially preserved by expanding this method to include the further steps of repetitively (d) backcrossing the insect-resistant progeny with insect-susceptible plants from the susceptible variety; and (e) selecting for expression of insect resistance (or an associated marker gene) among the progeny of the backcross, until the desired percentage of the characteristics of the susceptible variety are present in the progeny along with the gene imparting insect resistance. Subsequently, the inbreds according to this invention may be crossed with another inbred line to produce the hybrid.

The present invention further contemplates using, with the plant non-specific lipid acyl hydrolase, adjuvants, chemical or biological additives in an effort to expand the spectrum of target pests, to extend the duration of effectiveness of the plant non-specific lipid acyl hydrolase or to help stabilize the agricultural composition of the plant non-specific lipid acyl hydrolase. Exemplary potentiators would include lectins, amphipathic proteins or proteinase inhibitors.

The present invention contemplates protecting any plant of a taxon which is susceptible to infestation and damage by one or more of corn rootworms, potato beetles, armyworms, borers, cutworms, wireworms, earworms and aphids. By the term "taxon" herein is meant a unit, a botanical classification of genus or lower. It thus includes genus, species, cultivars, varieties, variants and other minor taxonomic groups which lack a consistent nomenclature.

Exemplary plants include maize, rice and potato. However, it is not to be construed as limiting, inasmuch as these insects may infest certain other crops. Thus, the methods of the invention are readily applicable to numerous plant species, if they are found to be susceptible to the plant species listed hereinabove, including without limitation, species from the genera Medicago, Trifolium, Vigna, Citrus, Daucus, Arabidopsis, Brassica, Raphanus, Sinapis, Capsicum, Lycopersicon, Nicotiana, Solanum, Helianthus, Bromus, Asparagus, Panicum, Pennisetum, Cucumis, Glycine, Lolium, Triticum and Zea.

EXAMPLES

The present invention is illustrated in further detail by the following examples. The examples are for the purposes of illustration only, and are not to be construed as limiting the scope of the present invention. All parts and percentages are by weight unless otherwise specifically noted. All DNA sequences are given in the conventional 5' to 3' direction. All amino acid sequences are given in conventional aminoterminus to carboxylic acid terminus direction.

Example 1

Purification of Patatins

Patatin was purified from tubers of the potato cutivars Atlantic, Superior, Desiree, Norcoda, Hilat, and LaChipper. Patatin purification was performed according to Racusen and Foote (1980), *J. Food Biochem.*, 4:43–52, and involved homogenization and ammonium sulfate fractionation then chromatography over DEAE cellulose and Concanavalin-A Sepharose. Yields of patatin were typically 20% of the total protein in the initial crude homogenate.

p-Nitrophenyl laurate (PNP-laurate) esterase activity was determined for patatin samples purified from different cultivars using a procedure adapted from Hofgen and Wilmitzer (*Plant Science* (1990) 66:221–230). In a 96 well microtiter plate, increasing amounts of patatin (0–10 μg) were added in a total volume of 0.05 ml 50 mM Tris, pH 8.5. 0.2 ml of a 3:1 diluted substrate (0.25 mM final concentration) was added to the protein samples and initial reaction rates were obtained by monitoring the production of para-nitrophenol at 405 nm using a Molecular Devices kinetic microplate reader. Esterase activity was calculated as the change in optical density per minute per μg protein.

The phospholipase activity of patatin was examined and quantified using a procedure modified from Hosteller, et al. (1991), *Methods Enzymol.*, 197:125–134. Reactions, performed at pH 8.5 and pH 5.5 for 20 and 45 minutes, respectively, contained 1 mM phosphatidylcholine which contained with L-3 phosphatidylcholine 1,2-di(1–14C) palmitoyl in a total volume of 0.2 ml. Reactions were stopped by adding 0.1 volumes glacial acetic acid, followed by a two volume chloroform-methanol (2:1). The samples were then vortexed and the aqueous and organic phases were allowed to separate. Both products and substrates were found in the organic phase. The organic phase was spotted on silica gel 60 TLC plates and products and reactants were separated using a solvent system consisting of heptane/diethyl ether/formic acid (90:60:4). Lipids were visualized with iodine vapors, removed from the plate, placed in scintillation cocktail and counted. Specific activities were calculated as nmols free fatty acid produced/min/mg protein. Values for the various cultivars tested ranged from 210 to 2,242 nmol free fatty acid produced/minute/mg protein. Analysis of the specific products indicated that patatin exhibited phospholipase B activity at pH 8.5 and pH 5.5 (i.e., both acyl groups were removed from phosphatidylcholine).

Example 2

Effect of Patatin on the Growth of Diabrotica Larvae 0.03 ml of purified patatin solution (in 25 mM sodium phosphate buffer, pH 7.2) was applied to the surface of 0.25 ml artificial diet (adapted from Rose and McCabe (1973), *J. Econ. Entomol.*, 66:398–400) in 24 well plates and allowed to air dry in a laminar flow hood. The wells were then infested with single, neonate southern corn rootworm (SCR, *Diabrotica undecimpunctata howardi*) hatched from sterilized eggs or with single, preweighed second instar SCR or western corn rootworm (WCR, *Diabrotica virgifera virgifera*). The plates were then placed in sterilized, sealed plastic containers and put in a humidified growth chamber maintained at 25° C. for 6 days (SCR) or 3.5 days (second instar SCR and WCR) prior to final weighing.

A. Effect on neonate SCR larvae

Increasing concentrations of purified patatin isolated from five potato cultivars (see Example 1) were used in feeding studies as described above. In all cases neonate SCR showed a dose dependent inhibition of growth upon ingestion of these patatins (Table 1). The maximal and 50% growth inhibition were similar for all patatins tested (66–84% inhibition of growth and 0.0625–0.125 mg/g diet, respectively).

TABLE 1

Effect of patatins isolated from different potato cultivars on growth of neonate southern corn rootworm larvae

| Treatment (mg/g diet) | CULTIVAR | | | | |
|---|---|---|---|---|---|
| | Atlantic | LaChipper | Hilat | Superior | Desiree |
| Control | 3.70 ± 0.19* | 3.88 ± 0.28 | 3.52 ± 0.21 | 3.19 ± 0.37 | 3.46 ± 0.29 |
| 0.03125 | 2.75 ± 0.23 | 2.38 | 3.05 ± 0.62 | 1.98 ± 0.49 | 1.99 ± 0.39 |
| 0.0625 | 2.49 ± 0.46 | 2.30 ± 0.55 | 2.18 ± 0.47 | 1.58 ± 0.50 | 1.88 ± 0.46 |
| 0.125 | 1.15 ± 0.19 | 1.48 ± 0.19 | 1.90 ± 0.33 | 1.21 ± 0.17 | 1.85 ± 0.46 |
| 0.25 | 0.93 ± 0.14 | 0.94 ± 0.11 | 1.17 ± 0.28 | 1.06 ± 0.21 | 1.27 ± 0.29 |
| 0.50 | 0.77 ± 0.18 | 0.64 | 0.88 | 1.10 ± 0.19 | 1.07 ± 0.10 |

*Values are the mean ± SEM for 2–9 separate experiments. Values without SEM are from 2 experiments.

These data demonstrate the ability of patatins from different cultivars to inhibit the growth of neonate SCR larvae.

B. Effect on second instar WCR and SCR larvae

Neonate WCR larvae cannot be readily bioassayed due to their inability to develop on artificial diet. However, second instar larvae will develop on artificial diet and feeding assays were conducted as described above. Patatin from the Hilat cultivar caused substantial growth inhibition at the dose tested (Table 2) and was greater than that seen with neonate SCR (53% vs 67% inhibition, respectively).

TABLE 2

Effect of patatin from the potato cultivar Hilat on the growth of second instar western corn rootworm larvae.

| TREATMENT | WEIGHT INCREASE | % INHIBITION |
|---|---|---|
| Control* | 6.72 ± 0.50** | — |
| Patatin (0.25)* | 1.17 ± 0.48 | 83 |

Mean starting weights, control WCR = 2.58 mg, Patatin WCR = 2.71 mg
**Values are the mean ± SEM for 24 observations Similar experiments with second instar SCR indicate that patatin is about half as effective at this developmental stage as compared to WCR.

TABLE 3

Effect of patatin from the potato cultivar Hilat on the growth of second instar southern corn rootworm larvae

| TREATMENT | WEIGHT INCREASE | % INHIBITION |
|---|---|---|
| Control* | 14.39 ± 0.90 | — |
| Patatin (0.25)* | 8.58 ± 0.6 | 40 |

Mean starting weights, control SCR = 2.49 mg; Patatin SCR = 2.61 mg

These data demonstrate that growth of WCR larvae is reduced upon ingestion of patatin and that WCR are more sensitive to patatin than SCR.

Example 4

Effect of an Isolated Isoform of Patatin on Neonate SCR Larvae

A single isoform of patatin from the cultivar Desiree was obtained by fractionating the purified multi-isoform material over a Pharmacia Mono-Q™ anion exchange column equilibrated in 20 mM Tris-HCl, pH 8.5. Proteins were eluted using a NaCl gradient from 0–500 mM over 1 hour. Each fraction of patatin was then examined by isoelectric focusing. The fractions containing the most basic isoform (pI=6.5) were combined, dialyzed against 25 mM sodium phosphate buffer and concentrated. This single isoform, designated Desiree-B, was then used in neonate SCR feeding studies (Table 4). A similar degree of growth inhibition was seen with the single isoform (Desiree-B) sample of patatin as with the multiple isoforms.

TABLE 4

Effect of multiple vs single isoforms of patatin from the potato cultivar Desiree on growth of neonate southern corn rootworm larvae

| TREATMENT (mg/g diet) | LARVAL WEIGHT (mg) |
|---|---|
| Control* | 3.98 ± 0.16* |
| Desiree (0.25) | 1.97 ± 0.22 |
| Desiree-B (0.25) | 1.39 ± 0.12 |

*Values are the mean ± SEM for two separate experiments

These data indicate that a single isoform of patatin is capable of producing growth inhibition of Diabrotica larvae, and that a complex mixture of isoforms is not essential for growth inhibition.

Example 5

Effect of Patatin Inactivated with Di-isopropyl Fluorophosphate on Neonate SCR

Inspection of the amino acid sequence of several patatins reveals that the serine hydrolase active site motif Gly-Xxx-Ser-Xxx-Gly is present in all the sequences, centered around Ser 77. Patatin therefore appears to be a member of the serine hydrolase class of enzymes. Consistent with this classification, patatin is completely inactivated by treatment with di-isopropyl fluorophosphate (DFP), the specific active site titrant of serine hydrolases. To establish whether the enzymatic activity of patatin is necessary for the effect on insect larval growth, patatin (17 mg) from the cultivar Atlantic was inactivated by treatment with a 10-fold molar excess of DFP. The mixture was placed on an orbital shaker at room temperature for 1 hour after which the excess DFP was removed by chromatography over a Pharmacia Fast™ desalting column equilibrated in 25 mM sodium phosphate buffer, pH 7.0. The resulting modified protein was concentrated, quantified and tested for esterase and phospholipase activity as described in Example 1. No esterase activity was apparent in patatin after treatment with DFP, whereas the unmodified protein had a specific activity of 21.5 mmOD/min/mg protein. The phospholipase activity of DFP-treated patatin was 19.8 (±5.0) nmols free fatty acid/min/mg protein compared to 2420 (±350) nmols free fatty acid/min/mg protein for untreated patatin.

The effect of DFP-treated patatin on the growth of neonate SCR was then determined. The DFP-treated patatin had little or no effect on Diabrotica larval growth at both 0.25 and 0.5 mg patatin/g diet (Table 5).

TABLE 5

Effect of DFP-treated patatin on neonate southern corn rootworm larvae

| TREATMENT (mg/g diet) | LARVAL WEIGHT (mg) |
|---|---|
| Experiment-A | |
| Control | 3.07 ± 0.31* |
| Patatin (0.5) | 0.62 ± 0.06 |
| DFP-treated Patatin | 3.81 ± 0.31 |
| Experiment-B | |
| Control | 4.28 ± 0.16 |
| Patatin (0.25) | 1.52 ± 0.26 |
| DFP-treated Patatin | 3.43 ± 0.33 |

*Values are the means ± SEM

These data indicate that the enzymatic activity of patatin is required for inhibition of Diabrotica larval growth.

Example 6

Protective Effect of Patatin Coated on Plant Leaves

Leaf coating experiments were performed using the method of Wolfson and Murdock (1987), supra. Leaf segments of 3 week old corn seedlings were dipped in a 20 mg/ml patatin solution in 5% gelatin maintained at 33° C., then allowed to air-dry. Control solutions contained no patatin. The leaves were then placed in a petri dish on moist filter paper and infested with 10 second instar western spotted cucumber beetle (WSCB, *Diabrotica undecimpunctata undecimpunctata*) larvae (mean initial weight; 3.3 mg). Each treatment was replicated 3 or 4 times. After 3 days, larval feeding damage of the leaves was estimated using the following rating:

5. ≧50% of the leaf consumed, heavy damage
4. ≧20% of the leaf consumed, significant damage
3. <20% of the leaf consumed, many areas show continued feeding with large holes.
2. Smaller holes, slower or interrupted feeding damage, 1-2 areas per leaf with damage.
1. Little feeding damage.

Results are shown in Table 6.

TABLE 6

Effect of Patatin of WSCB Larval Feeding

| Treatment | Mean Leaf Damage Rating (± standard error) |
|---|---|
| Control | 4 (±0.6) |
| Patatin | 2 (±0.4) |

Damage on Corn Leaves

The leaves coated with patatin showed significantly less damage than control leaves (p<0.05). This example shows that plant tissue is protected from Diabrotica feeding damage by patatin.

Example 7

Effect of Patatin on Colorado Potato Beetle Larval Growth

Potato leaflets were dipped in 10 mg/ml patatin in 5% gelatin maintained at 33° C. and allowed to air dry. The leaflets were placed in a petri dish containing moist filter paper and infested with 4 Colorado potato beetle (*Leptinotarsa decemlineata*) larvae (mean initial weight; 20.3 mg). Each treatment was replicated 3 times. After 3 days, the larvae were weighed and the results are shown in Table 7.

TABLE 7

Inhibition of Colorado Potato Beetle Larval Growth by Patatin

| Treatment | Mean weight gain, mg (± standard error) |
|---|---|
| Control | 33.7 (±4.1) |
| Patatin | 15.0 (±7.2) |

The Colorado potato beetle larvae grew significantly less on the patatin coated leaves ($p<0.05$). This example shows that another Coleopteran pest, Colorado potato beetle is also deleteriously affected by patatin.

Example 8

Effect of Patatin on Growth of Spodoptera Larvae 0.5 ml of 1 mg/ml patatin or 1 mg/ml bovine serum albumin (BSA) dissolved in water was mixed into 2 ml artificial diet dispensed in 24 well plates. Control wells were mixed with 0.5 ml water. The wells were each infested with one second-instar beet armyworm (*Spodoptera exigua*) larva (mean initial weight; 2 mg). After 5 days, the larvae were weighed. Results are shown in Table 8.

TABLE 8

Inhibition of Beet Armyworm Larval Growth by Patatin

| Treatment | n | Mean weight gain, mg (± standard error) |
|---|---|---|
| Control | 11 | 223 (±16.3) |
| + BSA | 12 | 222 (±16.0) |
| + Patatin | 22 | 176 (±13.0) |

The beet armyworm larvae on the patatin-treated diet were significantly smaller (21% inhibition of growth) than the larvae on the control diet and the diet treated with BSA ($p<0.05$).

Example 9

Effect of Patatin on Growth and Development of Borers, Cutworms, Wireworms and Aphids The effect of patatin on borers, cutworms, wireworms and aphids is determined by applying various amounts of patatin in or onto the insect food. This is accomplished using artificial diets as described in "The Handbook of Insect Rearing, Vols. 1 and 2 (1985), (eds.) P. Singh and R. F. Moore, Esevier Press, NY.

Alternatively, the protein is applied to the surface of appropriate plants or plant tissues by the method of Wolfson and Murdock, supra, as detailed in Examples 6 and 7. The deleterious effect of patatin on the insects is assessed after 1–5 days by measuring inhibition of growth and development or mortality. Alternatively, the plant material is scored for damage by the method described in Example 6.

Example 10

Isolation of Plant Non-specific Lipid Acyl Hydrolase from Phaseolus Leaves

The plant non-specific lipid acyl hydrolase found in leaves of runner bean *Phaseolus multifloris* is purified following the protocol described in Burns, et al. (1979), *Phytochem.*, 18:1793–1797. This involves heat treatment (50° C.) and sequential chromatography by DEAE-cellulose, Sephadex G-100 and hexyl-agarose. An alternative purification of plant non-specific lipid acyl hydrolase from leaves is performed by the procedure of Matsuda and Hiruyama (1979), *Biochim. Biophys., Acta.*, 573:155–165 which employs acetone treatment, Sephadex G-100™ and palmitoyl gauze chromatography and isoelectric focusing. The purified protein is biochemically assayed as described in Example 1 and the inhibitory effect of insect growth is demonstrated using assays described in Examples 2, 6, 7 and 8. Amino acid sequence data is determined by N-terminal sequencing of the purified polypeptides, or by sequencing oligopeptides generated by the proteolysis of the non-specific plant non-specific lipid acyl hydrolase using trypsin, chymotrypsin or other suitable enzymes and cleavage reagents. Antisera to the purified plant non-specific lipid acyl hydrolase are also generated by commercial vendors of this service, such as the Berkeley Antibody Company (Berkeley, Calif.).

Example 11

Construction of a cDNA Library from Potato Tuber Skin Tissue

A. RNA Purification

The skin and outer cortex tissue from 4 cm potato tubers (*Solanum tuberosum* cv. Superior) was harvested and immediately frozen in liquid nitrogen. Frozen tissue was ground in a mortar to a fine powder under liquid nitrogen. Five grams of tissue were extracted with a volume of 50 mM Tris-HCl pH 8.0, 4% para-amino salicylic acid, 1% triisopropylnapthalene-sulfonic acid, 10 mM dithrothreitol, and 10 mM sodium metabisulfite. The homogenate was then extracted with an equal volume of phenol containing 0.1% 8-hydroxyquinoline. After centrifugation the aqueous layer was extracted with an equal volume of phenol containing chloroform:isoamylalcohol (24:1), followed by extraction with chloroform:octanol (24:1). Subsequently, 7.5M ammonium acetate was added to a final concentration of 2.5M. The RNA was precipitated overnight at −20° C., collected by centrifugation, reprecipitated with 2.5M ammonium acetate and washed with 70% ethanol. The dried RNA was resuspended in water and stored at −80° C. Poly A⁺ RNA was isolated using Hybond mAP™ messenger affinity paper (Amersham).

B. cDNA Construction and Screening cDNA was synthesized using 5 µg of Poly A⁺ RNA and a ZAP-cDNA™ synthesis kit (Stratagene). Size-selected cDNA was ligated to 2 µg of UniZap XR™ vector arms (Stratagene), and packaged into phage particles with Gigapack Gold™ packaging extract (Stratagene). About $4.2 \times 10^6$ putative clones were obtained after packaging. The plate amplified library contained approximately $5.0 \times 10^{10}$ plaque forming units per milliliter (pfu/ml) when titered using *E. coli* PLK-F™ cells (Stratagene) as the host strain.

Example 12

Construction of Plant Expression Plasmids

The plasmid pDAB219A represents a dual purpose vector containing two genes, each under the control of a promoter expressed in callus tissue. The first gene, a screenable marker, is a modified beta-glucuronidase (gus) gene from *Escherichia coli* under the translational control of the Cauliflower Mosaic Virus 35S promoter. Plant transcription, termination and polyadenylation addition signals are supplied by sequences derived from the nopaline synthase gene. The second gene, bar, is a selectable marker which codes for phosphinothricine acetyl transferase and is derived from *Streptomyces hygroscopicus*. This gene is also under the regulation of the Cauliflower Mosaic Virus 35S promoter and nopaline synthase transcription termination polyadenylation sequences. The gus gene allows for the rapid analysis of expression using commercially available fluorometric or histochemical assays. The expression of the bar gene confers resistance to the herbicide Basta™ (Hoechst), thus, imparting a selective advantage to transformed cells under selection pressure. The sequences derived from Cauliflower Mosaic Virus (CaMV) represent the Cabb S strain. They are available as the MCASTRAS sequence of GenBank, and published by Franck et al. (1980), *Cell*, 21:285–294. A flow diagram showing the construction of plasmid pDAB219Δ is presented in FIGS. 4–8.

A. Plasmids utilizing the 35S promoter and the Agrobacterium Nos Poly A sequences The starting material is plasmid pBI221, purchased from CLONTECH (Palo Alto, Calif.). This plasmid contains a modified copy of the CaMV 35S promoter, as described in Bevan et al. (1985), *EMBO J.*, 4:1921–1926; Baulcombe et al. (1986), *Nature*, 321:446–449; Jefferson et al. (1987), *EMBO J.*, 6:3901–3907; and Jefferson (1987), *Plant Molec. Biol. Reporter*, 5:387–40. Beginning at the 3' end of the PstI site of pUC 19 (Yanisch-Perron et al. (1985), *Gene*, 33:103–119), and reading on the same strand as that which encodes the Lac Z gene of pUC 19, the promoter sequence is comprised of the linker nucleotides GTCCCC, followed by CaMV nucleotides 6605 to 7439, followed by the linker sequence GGGGACTCTAGAGGATCCCCGGGTGGT-CAGTCCCTT (SEQ. ID. NO. 5), wherein the underlined bases represent the BamHI recognition sequence. These bases are then followed by 1809 base pairs (bp) comprising the coding sequence of the *Escherichia coli* uidA gene, which encodes the b-glucuronidase (GUS) protein, and 44 bp of 3' flanking bases that are derived from the *E. coli* genome (Jefferson, et al. (1986), *Proc. Natl. Acad. Sci.*, 83:8447–8451), followed by the SstI linker sequence GAGCTC, which is then followed by the linker sequence GAATTTCCCC (SEQ. ID. NO. 6). These bases are followed by the RNA transcription termination/polyadenylation signal sequences derived from the *Agrobacterium tumefaciens* nopaline synthase (Nos) gene, and comprise the 256 bp Sau3AI fragment corresponding to nucleotides 1298 to 1554 of DePicker et al. (1982), (*J. Molec. Appl. Genet.*, 1:561–573), followed by two C residues, the EcoRI recognition sequence GAATTC, and the rest of pUC 19.

1. pBI221 DNA was digested with EcoRI and BamHI, and the 3506 bp fragment was separated from the 2163 bp small fragment by agarose gel electrophoresis, and then purified by standard methods. pRAJ275 (CLONTECH, Jefferson (1987), supra) DNA was digested with EcoRI and SalI, and the 1862 bp fragment was purified from an agarose gel. These two fragments were mixed together, and complementary synthetic oligonucleotides having the sequence GATCCGGATCCG (SEQ. ID. NO. 7) and TCGACGGATCCG (SEQ. ID. NO. 8) were added. The fragments were ligated together and the ligation reaction was transformed into competent *E. coli* cells. A transformant harboring a plasmid having the appropriate DNA structure was identified by restriction enzyme site mapping. This plasmid was named pKA881.

2. pKA881 DNA was digested with BalI and EcoRI, and the 4148 bp large fragment was purified from an agarose gel. DNA of pBI221 was similarly digested, and the 1517 bp EcoRI/BalI fragment was gel purified and ligated to the above pKA881 fragment, to generate plasmid pKA882.

3. pKA882 DNA was digested with SstI, the protruding ends were made blunt by treatment with T4 polymerase, and the fragment was ligated to synthetic BamHI linkers having the sequence CGGATCCG. An *E. coli* transformant that harbored a plasmid having BamHI fragments of 3784 and 1885 bp was identified and named pKA882B.

4. pKA882 DNA was digested with PstI, and the linear fragments were ligated to synthetic adaptors having the sequence CAGATCTGTGCA (SEQ. ID. NO. 9). An *E. coli* transformant was identified that harbored a plasmid that was not cleaved by PstI, and that had a new, unique BglII site. This plasmid was named pKA882-Bg.

5. pKA882-Bg DNA was digested with EcoRI, and the linear fragments were ligated to synthetic adaptors having the sequence AATTGAGATCTC (SEQ. ID. NO. 10). An *E. coli* transformant was identified that harbored a plasmid that was not cleaved by EcoRI, and that generated BglII fragments of 3027 and 2658 bp. This plasmid was named pKA882-2xBg.

6. pKA882B DNA was digested with BamHI and the mixture of fragments was ligated. An *E. coli* transformant harboring a plasmid that generated a single 3783 bp fragment upon digestion with BamHI was identified and named p35S/Nos. This plasmid has the essential DNA structure of pBI221, except that the coding sequences of the GUS gene have been deleted. Therefore, CaMV nucleotides 6605 to 7439 are followed by the linker sequence GGGGACTCTAGAGGATCCCGAATTTC-CCC (SEQ. ID. NO. 11), which is followed by the Nos polyadenylation sequences and the rest of pBI221.
7. p35S/Nos DNA was digested with EcoRV and PstI, and the 3037 bp fragment was purified and ligated to the 534 bp fragment obtained from digestion of p35S/En2 DNA (see Example 12, Section C.5) with EcoRV and PstI. An *E. coli* transformant was identified that harbored a plasmid that generated fragments of 3031 and 534 bp upon digestion with EcoRV and PstI, and the plasmid was named p35S En2/Nos. This plasmid contains the duplicated 35S promoter enhancer region described for p35S En2 in Example 12, Section C.5. The promoter sequences were separated from the Nos polyadenylation sequences by linker sequences that include a unique BamHI site.

B. Plasmids utilizing the 35S promoter and the Agrobacterium ORF 25/26 Poly A sequences The starting material is plasmid pIC 35. This plasmid contains the 845 bp SmaI/HindIII fragment from pUC 13 35S (-343) [see Example 12, Section C], ligated into the NruI and HindIII sites of pIC 19R (Marsh, et al. (1984), *Gene*, 32:481–485), in the orientation such that the HindIII recognition site is maintained. The source of the *A. tumefaciens* ORF25/26 sequences is plasmid pIC1925. This plasmid contains the 713 bp HincII fragment comprising nucleotides 21728 to 22440 of *A. tumefaciens* pTi 15955 T-DNA (Barker et al., *Plant Molec. Biol.*, 2:335–350), ligated into the SmaI site of pIC 19H (Marsh, et al. (1984), supra), in the orientation such that the BamHI site of pIC 19H is adjacent to the ORF 25 end of the T-DNA fragment.

1. DNA of plasmid pIC 35 was digested with BamHI, and ligated to a 738 bp fragment prepared by digestion of pIC1925 DNA with BamHI and BglII. An *E. coli* transformant was identified that harbored a plasmid in which a BamHI site was positioned between the 35S promoter fragment and the ORF 25/26 Poly A fragment. This plasmid was named pIC 19R35/A.
2. pIC 19R35/A DNA was digested with SmaI at its unique site, and the DNA was ligated to BglII linkers having the sequence CAGATCTG. The tandomization of these BglII linkers generates, besides BglII recognition sites, also PstI recognition sites, CTGCAG. An *E. coli* transformant was identified that had at least two copies of the linkers (and new BglII and PstI sites) at the position of the former SmaI site. This plasmid was named pIC35/A.
3. DNA of plasmid pIC 20R (Marsh, et al. (1984), *Gene*, 32:481–48514) was digested with NruI and SmaI, and the blunt ends of the large fragment were ligated together. An *E. coli* transformant was identified that harbored a plasmid that lacked NruI, SmaI, HindIII, SphI, PstI, SalI, XbaI, and BamHI sites. This plasmid was called pIC 20RD.
4. pIC 20RD DNA was digested with BglII, and was ligated to the 1625 bp BglII fragment of pIC35/A. An *E. coli* transformant was identified that harbored a plasmid that contained the 35S promoter/ORF 25 poly A sequences. Restriction enzyme site mapping revealed these sequences to be in the orientation such that the unique KpnI and XhoI sites of pIC 20RD are positioned at the 3' end of the ORF 25 Poly A sequences. This plasmid was named pSG Bgl 3525 (Pst).
5. DNA of pSG BglII 3525 (Pst) was digested with BglII under conditions in which only one of the two BglII sites of the molecule were cleaved. The 4301 bp linear fragments were ligated to synthetic adapter oligonucleotides having the sequence GATCGTGATCAC (SEQ. ID. NO. 12), where the underlined bases represent the BclI recognition sequence. An *E. coli* transformant was identified that had a BclI site at the position of the former BglII site positioned 5' to the 35S promoter. This plasmid was named pSG 3525 a (Pst).

C. Construction of a doubly-enhanced CaMV 35S Promoter

The starting material is plasmid pUC13/35S (-343) as described by Odell et al. ((1985), *Nature*, 313:810–812). This plasmid comprises, starting at the 3' end of the SmaI site of pUC 13 (Messing, J. (1983) in "Methods in Enzymology" (Wu, R. et al., Eds) 101:20–78), and reading on the strand contiguous to the noncoding strand of the Lac Z gene of pUC 13, nucleotides 6495 to 6972 of CaMV, followed by the linker sequence CATCGATG (which encodes a ClaI recognition site), followed by CaMV nucleotides 7089 to 7443, followed by the linker sequence CAAGCTTG, the latter sequence including the recognition sequence for HindIII, which is then followed by the remainder of the pUC 13 plasmid DNA.

1. pUC 13/35S (-343) DNA was digested with ClaI, and the protruding ends were made flush by treatment with T4 polymerase. The blunt-ended DNA was then ligated to synthetic oligonucleotide linkers having the sequence CCCATGGG, which includes an NcoI recognition site. An *E. coli* transformant was identified containing a plasmid (named pOO#1) having an NcoI site positioned at the former ClaI site.
2. pOO#1 DNA was digested with NcoI and the compatible ends of the large fragment were religated, resulting in the deletion of 70 bp from pOO#1, to generate plasmid pOO#1 NcoΔ.
3. pOO#1 NcoΔ DNA was digested with EcoRV, and the blunt ends were ligated to ClaI linkers having the sequence CATCGATG. An *E. coli* transformant harboring a plasmid having a new ClaI site at the position of the previous EcoRV site was identified, and the plasmid was named pOO#1 NcoΔRV/Cla.
4. pOO#1 NcoΔ RV/Cla DNA was digested with ClaI and NcoI, and the small (268 bp) fragment was purified from an agarose gel. This fragment was then ligated to the 3429 bp ClaI/NcoI fragment of pUC 13/35S (-343) prepared by isolation from an agarose gel, and an *E. coli* transformant was identified that harbored a plasmid having ClaI/NcoI fragments 3429 and 268 bp. This plasmid was named pUC 13/35S En.
5. pUC 13/35S En DNA was digested with NcoI, and the protruding ends were made blunt by treatment with T4 polymerase. The treated DNA was then cut with SmaI, and was ligated to BglII linkers having the sequence CAGATCTG. An *E. coli* transformant was identified that harbored a plasmid in which the 416 bp SmaI/NcoI fragment had been replaced with at least two copies of the BglII linkers and named p35S En$^2$.

The DNA structure of p35S En$^2$ is as follows: beginning with the nucleotide that follows the third C residue of the SmaI site on the strand contiguous to the noncoding strand of the Lac Z gene of pUC 13; the linker sequence CAGATCTGCAGATCTGCATGGGCGATG (SEQ. ID. NO. 13), followed by a CaMV nucleotides 7090 to 7344, followed by a ClaI linker sequence CATCGATG, followed by CaMV nucleotides 7089 to 7443, followed by the HindIII linker sequence CAAGCTT, followed by the rest of pUC 13 sequence. This structure has the feature that the enhancer sequences of the CaMV 35S promoter, which lie in the region upstream of the ECORV site in the viral genome (nucleotides 7090 to 7344), have been duplicated. This promoter construct incorporates the native 35S transcription start site, which lies 11 nucleotides upstream of the first A residue of the HindIII site.

D. Construction of a synthetic untranslated leader

A DNA fragment was constructed that includes sequences which comprise the 5' untranslated leader portion of the major rightward transcript of the Maize Streak Virus (MSV) genome. The MSV genomic sequence was published by Mullineaux et al., (1984), *EMBO J.*, 3:3063–3068, and Howell (1984), *Nucl. Acids Res.*, 12:7359–7375, and the transcript was described by Fenoll et al. (1988), *EMBO J.*, 7:1589–1596. The entire sequence, comprising 154 bp, was constructed in three stages by assembling blocks (A, B, and C) of synthetic oligonucleotides.

1. The A Block: Complementary oligonucleotides having the sequence

GATCCAGCTGAAGGCTCGACAAGGCA-
GATCCACGGAGGAGCTGA TATTTGGT-
GGACA                                (SEQ. ID. NO. 14)

and

AGCTTGTCCACCAAATATCAGCTCCTCCGTGGATC TGCCT-
TGTCGAGCCTTCAGCTG                    (SEQ. ID. NO. 15)

were synthesized and purified by standard procedures. Annealing of these nucleotides into double-stranded structures leaves 4-base sticky ends that are compatible with those generated by BamHI on one end of the molecule (GATC), and with HindIII-generated single stranded ends on the other end of the molecule (AGCT). Such annealed molecules were ligated into plasmid pBluescript SK(–) [Stratagene Cloning Systems, La Jolla, Calif.], that had been digested with BamHI and HindIII. An *E. coli* transformant harboring a plasmid containing the oligonucleotide sequence was identified by BamHI and HindIII restriction enzyme analysis, and the plasmid was named pMSV A.

2. The B Block: Complementary oligonucleotides having the sequences

AGCTGTGGATAGGAGCAACCCTATC-
CCTAATATACCAGCACCA CCAAGTCAGGGCAATC-
CCGGG                                (SEQ. ID. NO. 16)

and

TCGACCCGGGATTGCCCTGACTTGGTGG TGCTGGTATATT-
AGGGATAGGGTTGCTCCTATCCAC            (SEQ. ID. NO. 17)

were synthesized and purified by standard procedures. The underlined bases represent the recognition sequence for restriction enzymes SmaI and XmaI. Annealing of these nucleotides into double-stranded structures leaves 4-base sticky ends that are compatible with those generated by HindIII on one end of the molecule (AGCT), and with SalI-generated sticky ends on the other end of the molecule (TCGA).

DNA of pMSV A was digested with HindIII and SalI, and was ligated to the above annealed oligonucleotides. An *E. coli* transformant harboring a plasmid containing the new oligonucleotides was identified by restriction enzyme site mapping, and was named PMSV AB.

3. The C Block: Complementary oligonucleotides having the sequences

CCGGGCCATTTGTTCCAGGCACGGGATAAGCA TTCAGC-
CATGGG ATATCAAGCTTGGATCCC         (SEQ. ID. NO. 18)

and

TCGAGGGATCCAAGCTTGATATCCCATGGC TGAATGCT-
TATCCCGTGCCTGGAACAAATGGC            (SEQ. ID. NO. 19)

were synthesized and purified by standard procedures. These oligonucleotides incorporate bases that comprise recognition sites (underlined) for NcoI (CCATGG), EcoRV (GATATC), HindIII (AAGCTT), and BamHI (GGATCC). Annealing of these nucleotides into double-stranded structures leaves 4-base sticky ends that are compatible with those generated by XmaI on one end of the molecule (CCGG), and with XhoI-generated sticky ends on the other end of the molecule (TCGA). Such annealed molecules were ligated into pMSV AB DNA that had been digested with XmaI and XhoI. An *E. coli* transformant harboring a plasmid containing the oligonucleotide sequence was identified by restriction enzyme site analysis, and DNA structure was verified by sequence analysis. The plasmid was named pMSV CPL; it contains the A, B and C blocks of nucleotides in sequential order ABC. Together, these comprise the 5' untranslated leader sequence ("L") of the MSV coat protein ("CP") gene. These correspond to nucleotides 167 to 186, and nucleotides 188 to 317 of the MSV sequence of Mullineaux et al., (1984), supra, and are flanked on the 5' end by the BamHI linker sequence GGATCCAG, and on the 3' end by the linker sequence GATATCAAGCTTGGATCCC (SEQ. ID. NO. 20). An A residue corresponding to base 187 of the wild type MSV sequence was inadvertently deleted during cloning.

4. BglII Site Insertion pMSV CPL DNA was digested at the SmaI site corresponding to base 277 of the MSV genomic sequence (Mullineaux, et al. (1984), supra), and the DNA was ligated to BglII linkers having the sequence CAGATCTG. An *E. coli* transformant harboring a plasmid having a unique BglII site at the position of the former SmaI site was identified and verified by DNA sequence analysis, and the plasmid was named pCPL-Bgl.

E. Construction of a deleted version of the maize alcohol dehydrogenase 1 (Adh1) intron 1

The starting material is plasmid pVW119. This plasmid contains the DNA sequence of the maize Adh 1.S gene intron 1 from nucleotides 119 to 672, and was described in Callis et al. (1987), *Genes and Devel.*, 1:1183–1200. The sequence following base 672 of Dennis et al. ((1984), *Nucl. Acids Res.*, 12:3983–4000) is GACGGATCC, where the underlined bases represent a BamHI recognition site. The entire intron 1 sequence, including 14 bp of exon 1, and 9 bp of exon 2, was obtained from this plasmid on a 556 bp fragment following digestion with BclI and BamHI.

1. Plasmid pSG 3525 a (Pst) DNA (see Example 12, Section B.5) was digested with BamHI and BclI, and the 3430 bp fragment was purified from an agarose gel. pVW119 DNA was digested with BamHI and BclI, and the gel purified fragment of 556 bp was ligated to the above 3430 bp fragment. An *E. coli* transformant was identified that harbored a plasmid that generated fragments of 3430 and 556 bp upon digestion with BamHI and BclI. This plasmid was named pSG Adh A1.

2. pSG Adh A1 DNA was digested with HindIII, [which cuts between bases 209 and 210 of the Dennis et al. ((1984), supra) sequence, bottom strand], and with StuI, which cuts between bases 554 and 555. The ends were made flush by T4 polymerase treatment, and then ligated. An *E. coli* transformant harboring a plasmid lacking HindIII and StuI sites was identified, and the DNA structure was verified by sequence analysis. The plasmid was named pSG Adh A1D. In this construct, 344 bp of DNA have been deleted from the interior of the intron 1. The functional intron sequences is obtained on a 213 bp fragment following digestion with BclI and BamHI.

3. pCPL-Bgl DNA (see Example 12, section D.4), was digested with BglII, and the linearized DNA was ligated to the 213 bp BclI/BamHI fragment containing the deleted version of the Adh 1.S intron 1 sequences from pSG Adh A1D. An *E. coli* transformant was identified by restriction enzyme site mapping that harbored a plasmid containing the intron sequences ligated into the BglII site, in the orientation such that the BglII/BclI juncture was nearest the 5' end of the MSV CPL leader sequence, and the BglII/BamHI juncture was nearest the 3' end of the CPL. This orientation was confirmed by DNA sequence analysis. The plasmid was named pCPL A1I1D. The MSV leader/intron sequences is obtained from this plasmid by digestion with BamHI and NcoI, and purification of the 373 bp fragment.

F. Construction of plant expression vectors based on the enhanced 35S promoter, the MSV CPL, and the deleted version of the Adh 1 intron 1

1. DNA of plasmid p35S En2/Nos (see Example 12, Section A.7) was digested with BamHI, and the 3562 bp linear fragment was ligated to a 171 bp fragment prepared from pMSV CPL DNA digested with BamHI. This fragment contains the entire MSV CPL sequence described in Section D.3. An *E. coli* transformant was identified by restriction enzyme site mapping that harbored a plasmid that contained these sequences in an orientation such that the NcoI site was positioned near the Nos Poly A sequences. This plasmid was named p35S En2 CPL/Nos. It contains the enhanced version of the 35S promoter directly contiguous to the MSV leader sequences, such that the derived transcript will include the MSV sequences in its 5' untranslated portion.

2. DNA of plasmid pKA882 (see Example 12, Section A.2) was digested with HindIII and NcoI, and the large 4778 bp fragment was ligated to an 802 bp HindIII/NcoI fragment containing the enhanced 35S promoter sequences and MSV leader sequences from p35S En2 CPL/Nos. An *E. coli* transformant harboring a plasmid that contained fragments of 4778 and 802 bp following digestion with HindIII and NcoI was identified, and named pDAB 310. In this plasmid, the enhanced version of the 35S promoter is used to control expression of the GUS gene. The 5' untranslated leader portion of the transcript contains the leader sequence of the MSV coat protein gene.

3. DNA of plasmid pDAB 310 was digested with NcoI and SstI. The large 3717 bp fragment was purified from an agarose gel and ligated to complementary synthetic oligonucleotides having the sequences CGGTACCTC-GAGTTAAC (SEQ. ID. NO. 21) and CATGGT-TAACTCGAGGTACCGAGCT (SEQ. ID. NO. 22). These oligonucleotides, when annealed into double stranded structures, generate molecules having sticky ends compatible with those left by SstI (AGCT), on one end of the molecule, and with NcoI (CATG) on the other end of the molecule. An *E. coli* transformant was identified that harbored a plasmid containing sites for enzymes SstI (AGCT), NcoI (CATG), KpnI (GGTACC), XhoI (CTCGAG), and HpaI (GTTAAC), and the DNA structure was verified by sequence analysis. This plasmid was named pDAB 1148.

Figure 9:
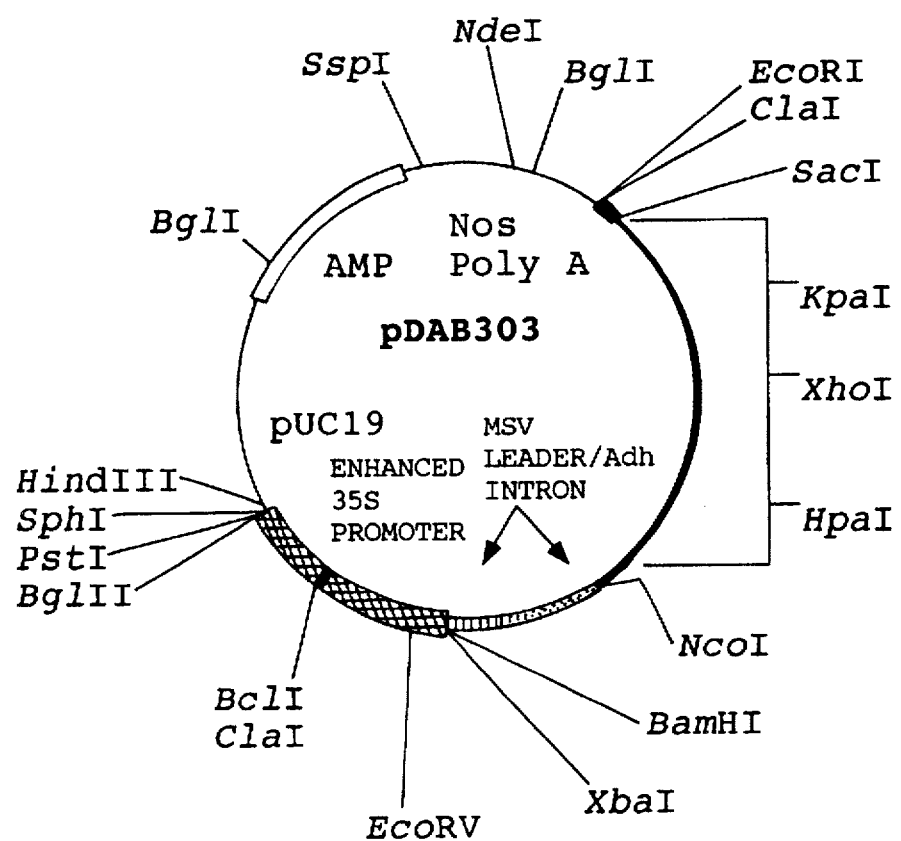
FIG. 9 shows a partial plasmid map of pDAB303.

4. DNA of plasmid pDAB 1148 was digested with BamHI and NcoI, the large 3577 bp fragment was purified from an agarose gel and ligated to a 373 bp fragment purified from pCPL A1I1D (See Example 12, Section E.3) following digestion with BamHI and NcoI. An *E. coli* transformant was identified that harbored a plasmid that generated fragments of 3577 and 373 bp following digestion with BamHI and NcoI, and the plasmid was named pDAB 303. A partial plasmid map of pDAB303 is set forth in FIG. 9. This includes a promoter, shown in FIGS. 10A–10B, comprising the doubly-enhanced CaMV 35S sequence (bases 19–656), and the deleted ADH1 sequence (bases 769–989) inserted into the MSV leader sequence (bases 657–768 and 990–1026). This plasmid has the following DNA structure: beginning with the base after final G residue of the PstI site of pUC 19 (base 435, see Messing, J. (1983) in *Methods in Enzymology*, Wu, R. et al. (eds) 101:20–78), and reading on the strand contiguous to the coding strand of the Lac Z gene, the linker sequence ATCTGCATGGGTG (SEQ. ID. NO. 23), nucleotides 7093 to 7344 of CaMV DNA, the linker sequence CATCGATG, nucleotides 7093 to 7439 of CaMV, the linker sequence GGGGACTCTAGAGGATCCAG (SEQ. ID. NO. 24), nucleotides 167 to 186 of MSV, nucleotides 188 to 277 of MSV, a C residue followed by nucleotides 269 to 359 of Adh 1S intron 1, nucleotides 704 to 821 of maize Adh S intron 1, the linker sequence GACG-GATCTG (SEQ. ID. NO. 25), nucleotides 278 to 317 of MSV, the linker sequence GTTAACTCGAGGTAC-CGAGCTCGAATTTCCCC (SEQ. ID. NO. 26), nucleotides 1298 to 1554 of Nos, and a G residue followed by the rest of the pUC 19 sequence. (including the EcoRI site).

G. Construction of plant transformation vectors containing the bar gene of *Streptomyces hygroscopicus*

The starting material is plasmid pIJ4104 (White, et al. (1990), *Nucl. Acids Res.*, 18:1062), which contains the coding region of the bar gene of *S. hygroscopicus*, which encodes the enzyme phosphinothricin acetyl transferase (PAT).

1. DNA of plasmid pIJ4104 was digested with SmaI, and the 569 bp fragment was purified from an agarose gel. DNA of plasmid pSG 3525 a (Pst) (see Example 12, Section B.5) was linearized by digestion at the unique HincII that lies between the 35S promoter and ORF 25 poly A sequences, and the linear fragment was ligated to the 569 bp bar gene fragment. An *E. coli* transformant was identified by restriction enzyme site mapping that harbored a plasmid containing the bar gene in the orientation such that BglII digestion generated fragments of 4118 and 764 bp. This plasmid was named pDAB 218.

2. DNA of plasmid PDAB 218 was digested with BclI, and the linear fragment of 4882 bp was ligated to a 3133 bp BglII fragment prepared from DNA of pKA882-2xBg (see Example 12, Section A.5). The latter fragment contains the GUS coding region, under the transcriptional control of the 35S promoter, with the Nos Poly A transcription termination signals. An *E. coli* transformant was identified that contained the GUS and PAT coding regions, and restriction enzyme recognition site mapping revealed that both coding regions were encoded by the same DNA strand. This plasmid was named pDAB 219.

3. DNA of plasmid pDAB 219 was used as the template for the polymerase chain reaction (Saiki et al., (1988), *Science*, 239:487–491) using as primers the synthetic oligonucleotides: i) CTCGAGATCTAGATATCGAT-GAATTCCC (SEQ. ID. NO. 27), and ii) TATGGATCCT-GTGATAACCGACATATGCCCCGGTTTCGTTG (SEQ. ID. NO. 28). Primer i) represents nucleotides 419 to 446 of pDAB 219, and includes bases corresponding to the recognition sites of XhoI (CTCGAG), BglII (AGATCT), XbaI (TCTAGA), EcoRV (GATATC), ClaI (ATCGAT), and EcoRI (GAATTC). The single underlined bases in primer ii) represent the recognition sequence of BamHI, and the double underlined bases represent nucleotides 1138 to 1159 of pDAB 219, and correspond to nucleotides 21728 to 21749 of the ORF 25 Poly A fragment (see, Example 5, Section B). PCR amplification generated a product of 760 bp.

4. DNA of plasmid pDAB 219 was digested with BglII, the 7252 bp fragment was purified from an agarose gel, and ligated to the 747 bp fragment generated by digestion of the above PCR product by BglII and BamHI. An *E. coli* transformant was identified that harbored a plasmid containing a unique BglII site positioned at the 3' end of the ORF 25 Poly A fragment. The DNA structure of the 3' end of the PAT coding sequence was confirmed by DNA sequence analysis. This plasmid was named PDAB 219Δ.

Figure 11:
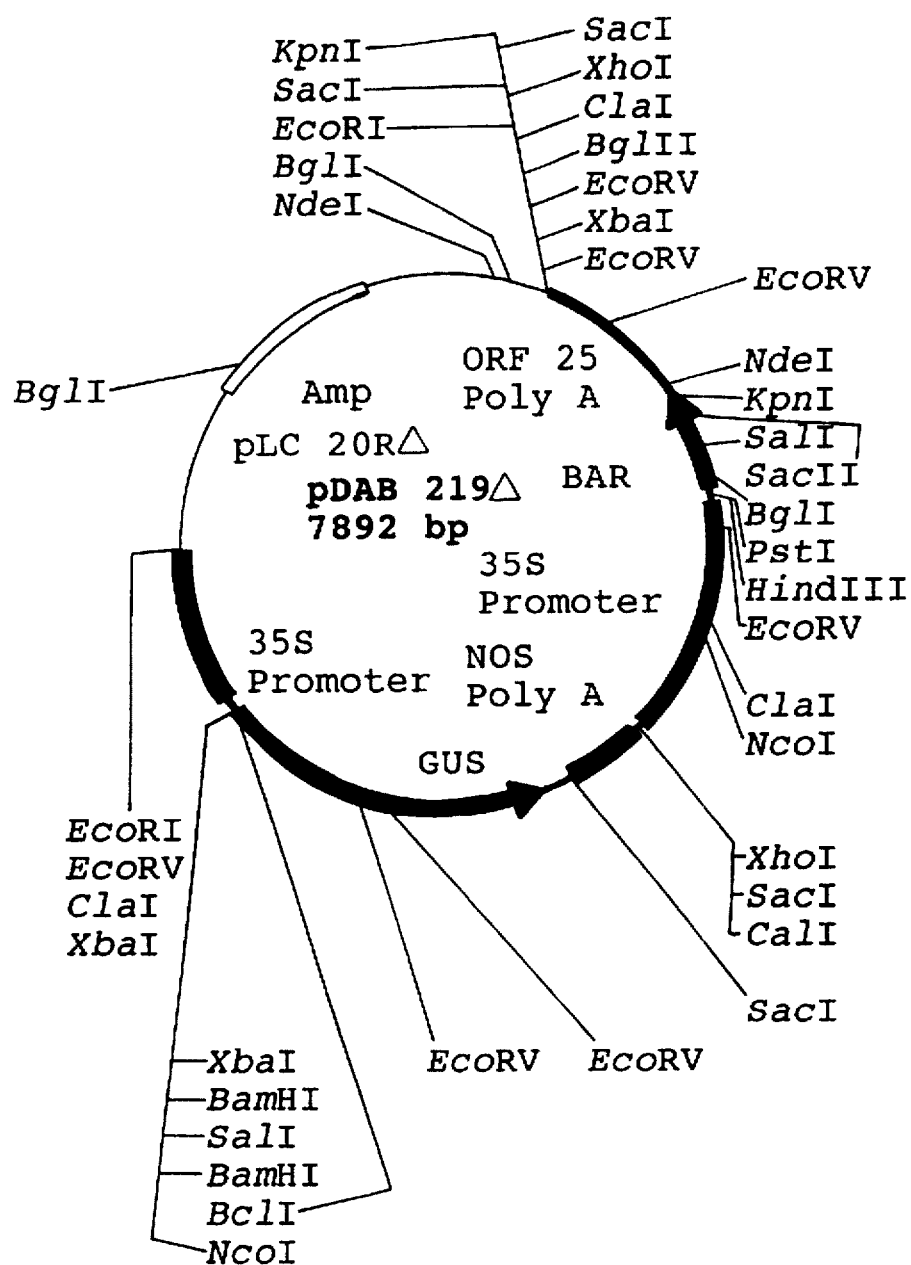
FIG. 11 shows a partial plasmid map of pDAB219Δ.

The DNA sequence of pDAB 219Δ is as follows: Beginning with the base following the last A residue of the XbaI site on the Lac Z coding strand of pIC 20R (Marsh, et al. (1984), *Gene*, 32:481–485), the linker TCCTGATCTGTG-CAGGTCCCC (SEQ. ID. NO. 29), followed by CaMV nucleotides 6605 to 7439, followed by the linker sequence GGGGACTCTAGAGGATCCGGATCCGTC-GACATGGTC (SEQ. ID. NO. 30), followed by the rest of the coding region of GUS with 44 bp of 3' flanking *E. coli* genomic DNA (nucleotides 306 to 2152 of Jefferson et al. (1986), *Proc. Natl. Acad. Sci.*, 83:8447–8451). The underlined bases represent the codons for the first two amino acids of the GUS protein, the second of which was changed from leucine in the original *E. coli* uidA gene (Jefferson et al. (1986), supra) to valine in pRAJ275 (Jefferson, (1987), supra). These bases are followed by the linker sequence GGGGAATTGGAGAGCTCGAATTTCCCC (SEQ. ID. NO. 31), then by bases 1298 to 1554 of the Nos Poly A sequence (DePicker, et al. (1982), *J. Molec. Appl. Genet.*, 1:561–5736). The linker sequence GGGAATTGAGAT-CAGGATCTCGAGCTCGGG (SEQ. ID. NO. 32) is followed by bases 495 to 6972 of CaMV, the linker CATCGATG, and CaMV bases 7090 to 7443. These bases are followed by the linker CAAGCTTGGCTGCAGGTC (SEQ. ID. NO. 47), then by bases corresponding to nucleotides 20 to 579 of the bar clone in pIJ4104 (White, et al. (1990), *Nucl. Acids Res.*, 18:1062), the linker CTGT-GATAACC (SEQ. ID. NO. 48), ORF 25/26 poly A nucleotides 21728 to 22440 (Barker, et al. (1983), *Plant Molec. Biol.*, 2:335–3501), the linker GGGAATTCATC-GATATCTAGATCTCGAGCTCGGGGTAC-CGAGCTCGAATTC (SEQ. ID. NO. 33), and the rest of pIC 20R. The BglII recognition site (underlined) represents a unique site into which other genes may be introduced. A partial restriction map of pDAB 219A is appended (see FIG. 11).

Example 13

Isolation of a gene coding for prepatatin

Amplified potato tuber cDNA libraries were plated on *E. coli* PLK-F, as described in Stratagene's Uni-Zap™ phage manual. Only a low density, of about 3000 phage per plate (80 mm dia), were used because a high proportion of hybridizing plaques was anticipated. The plaques were transferred to Nytran™ filters (Schleicher & Schuell, Keene, N.H.) and fixed by UV irradiation in a Stratalinker™ apparatus (Stratagene). The filters were probed with a 35-base oligonucleotide, which was complementary to positions 96–131 from the start of the patatin coding sequence:

GGAATGATTCCTTAATTCCACCTCCA-TCAATACT (SEQ. ID. NO. 34).

This region is highly conserved in eight published sequences of patatin cDNAs or genes (Bevan, et al. (1986), *Nucl Acid Res*, 14:4625–4638; Mignery, et al. (1984), *Nucl Acid Res*, 12:7987–8000; and Twell and Ooms (1988), supra). The probe was 3'-end labeled with digoxygenin-11-dUTP using terminal transferase (Boehringer-Mannheim, Indianapolis, Ind.). Filters were hybridized according to the manufacturer's protocols, with stringent washes in 2×SSC, 0.1% SDS at 65° C. ($T_m-8°$ C.). Binding was detected with antidigoxygenin antibody coupled to alkaline phosphatase (Boehringer-Mannheim). Approximately 2% of the library plaques hybridized to the patatin oligonucleotide. Four plaques were purified by 2 or 3 cycles of plating at low density and reprobing. The cDNAs were then excised as phagemids, by co-infecting with the phage and a helper phage (R408), as described in the Stratagene Uni-Zap™ Manual. An extra step of retransformation at low density was necessary to eliminate helper from the phagemids. Samples of phagemid DNA were prepared from XL1-Blue™ cells (Stratagene) by the method of Holmes and Quigley (1981), *Anal Biochem*, 114:193–197, and sequenced using a Sequenase™ kit (US Biochemical, Cleveland, Ohio).

The complete DNA sequence of the insert in clone pDAB1008 was determined (see FIG. 1). It is homologous to published patatin cDNAs (e.g. Mignery et al. (1984)), supra, except that the first 5 codons are missing. An oligonucleotide coding for the first 22 amino acids for prepatatin was synthesized. Its sequence was identical to that of pDAB1008, except that it included the 5 codons which are missing in the cDNA. These codons are identical to those in published patatin sequences (Bevan et al. (1986), supra; Mignery et al. (1984), supra; Twell & Ooms (1988), supra). The initiator ATG was incorporated into a NcoI site, and additional cloning sites were added downstream of the AflIII site (underlined): CATGGCAACTACT AAATCTTTTT-TAATTTTATTTTTTATGATATTAGCAAC-TACTAGTTCAACATG TTAACGGTACCCGGGC-CATGGA (SEQ. ID. NO. 35). In order to use this AflIII site for adding the rest of the patatin sequence, a vector lacking additional AflIII sites was required. This was prepared from pKK233-2 (Pharmacia, Piscataway, N.J.) by cutting with AflIII, filling-in the ends with Klenow fragment of DNA polymerase I, and recircularizing the plasmid with T4 DNA ligase. Enzymes were used according to the manufacturer's protocols. The oligonucleotide and its complement (AGCTTCCATGGCCCGGGTACCGTTAACATGTTG-AACTAGTAGTTGCTAATATCAA AAAATAAAAT-TAAAAAAGATTTAGTAGTTGC (SEQ. ID. NO. 36)) were then cloned into this derivative, between the NcoI and HindIII sites, to generate pDAB1079. The remainder of the patatin coding sequence, with 3'-non-coding sequences, was cloned into pDAB1079 on an AflIII-KpnI fragment from pDAB1008. The resulting plasmid, pDAB1126, encodes a prepatatin with the amino-terminal sequence (SEQ. ID. NO. 37) and is compared with the amino-terminal sequence of pDAB1008 (amino acid residues 6–30 of SEQ. ID. NO. 37):

pDAB1126: MATTKSFLILFFMILATTSSTCAKLEEMVT . . .

cf.pDAB1008: . . . . SFLILFFMILATTSSTCAKLEEMVT . . .

It includes the 23 amino acid amino-terminal signal which, in plant cells, directs the nascent polypeptide into the endoplasmic reticulum (ER) (Kirschner & Hahn (1986), *Planta*, 168:386–389). Mature patatin does not contain this signal, which is removed during entry into the ER.

The complete prepatatin sequence was transferred on a NcoI-XhoI fragment into the plant expression vector, pDAB303, which added a promoter, intron and transcription terminator for expression in corn cells. The resultant plasmid, pDAB1199, was introduced into protoplasts of cultured corn cells, where it directed synthesis of the expected 40 kD polypeptide which cross-reacted specifically with anti-patatin antiserum. The unique EcoRI site of pDAB1199 was converted to a BglII, site by the insertion of the oligonucleotide AATTGAGATCTC (SEQ. ID. NO. 49). The entire prepatatin gene (promoter, coding region and transcription terminator) was then cloned into another vector for plant transformation, pDAB219A, to generate pDAB1292.

Example 14

Patatin Expression in the Cytosol of a Plant Cell

Proteins which lack an amino-terminal signal for entry into the ER accumulate in the cytosol. The amount of protein accumulated in the cytosol may be higher (Denecke, et al (1990), *Plant Cell*, 2:51–59), or lower (Hiatt, et al. (1989), *Nature*, 342, 76–78), than in other subcellular compartments. Cytosolic patatin has been produced in transformed tobacco plants, but its abundance was not reported (unpubl. res. of Sonnewald, cited in Sonnewald, et al. (1990), *Plant Cell*, 2:345–355). Proteins are glycosylated in ER, but not in the cytosol.

DNA coding for cytosolic patatin was produced from pDAB1008 in PCR amplification (Perkin-Elmer, Norwalk, Conn.), using 25 cycles of 1 minute at 94° C., 1 minute at 50° C. and 3 minutes at 72° C. The 5' primer replaced the amino-terminal lysine of mature patatin with a dipeptide containing an initiator methionine and alanine. It also added a number of upstream restriction enzyme sites, including a NcoI site around the initiator ATG (underlined):

GCTCTAGAACTAGTGGATCCATGGCGT-
TGGAAGAAATGGTGCTG            (SEQ. ID. NO. 38).

The 3' primer (CTTTTCCCAGTCACGAC (SEQ. ID. NO. 39)) annealed to vector sequences downstream of the cloning site. Amplified DNA was cloned into pCR1000 (Invitrogen, San Diego, Calif.).

A gene for producing cytosolic patatin in plants was then assembled by cloning a NcoI-XhoI fragment into pDAB303, generating pDAB1194. This plasmid codes for a patatin with the amino-terminus (SEQ. ID. NO. 40) and is compared with the amino-terminal sequence of pDAB1008 (SEQ. ID. NO. 41):

pDAB1194: MALEEMVTVLSIDGGGIKGIIPAT ...

cf.pDAB1008: KLEEMVTVLSIDGGGIKGIIPAT ...

Example 15

A Gene for a Diverged Patatin

A second patatin cDNA, coding for a different protein isoform, was isolated and modified for expression in corn. In addition to the clones described in Example 13, clones were selected from the tuber cDNA library by their ability to produce protein which cross-reacted with anti-patatin serum. Antibody-binding to plaques on filters was detected with anti-rabbit antibody conjugated to alkaline phosphatase (Promega), according to the manufacturer's protocol.

Partial sequences at the 5' ends of these cDNAs were determined; pDAB1011 was most diverged from the sequence in pDAB1008 and was completely sequenced. The coding sequences of these two clones are 95.5% identical, but the differences translate into polypeptides which are only 88% identical. Both include most of an amino-terminal signal peptide, with the composition expected for ER entry (Chrispeels (1991), supra) . As seen in FIG. 2, the serine at amino acid 77 is presumed to be part of the lipid acyl hydrolase active site (by comparison with other hydrolases, Brady, et al. (1990), *Nature*, 343:767–770). Not surprisingly, the region around this serine is highly conserved. On the other hand, potential glycosylation sites (NXS/T) were not well conserved. The site at residue 115 is common to both, but pDAB1008 has a second site at position 382, whereas the second site is pDAB1011 is amino acid 203.

DNA coding for a cytosolic patatin was produced from pDAB1011 by PCR amplification, as described in Example 13. The NcoI-XhoI fragment was cloned into pDAB303, to generate pDAB1260.

The ER signal in pDAB1079 was completed by cloning the oligonucleotides CATGTGCCATGG (SEQ. ID. NO. 42) and AGCTTCCATGGCA (SEQ. ID. NO. 43) (Oligos etc.) between the AflIII and HindIII. They add the last codon, followed by an NcoI site containing an in-frame ATG codon. The complete signal, on an NcoI fragment, was introduced in front of the patatin-coding sequence in pDAB1260, to produce pDAB1274. The prepatatin encoded by this construct has the following amino-terminal sequence (SEQ. ID. NO. 44) and is compared with the amino-terminal sequence of pDAB1011 (SEQ. ID. NO. 45):

pDAB1274: MATTKSFLILFFMILATTSSTCAMALEEMVT ...

cf.pDAB1011: ... KSVLVLFFMILATTSSTCA-TLGEMVT ...

Example 16

Development of a Transgenic Maize Plant Expressing a Plant Non-specific Lipid Acyl Hydrolase A. Establishment of Friable, Embryogenic Callus Cultures Friable, embryogenic maize callus are initiated from immature embryos of the genotype B73×A188. Seed of the dent-corn inbred, B73, and the sweet-corn inbred, A188, are obtained from Holden's Foundation Seeds, Inc., Williamsburg, Iowa and the University of Minnesota, Crop Improvement Association, St. Paul, Minn., respectively. Seed are sown individually in pots containing approximately 18 kg of dry soil mix (Conrad Fafard, Inc., Springfield, Mass.) moistened and adjusted to pH 6.0. The plants are maintained in a greenhouse under a 16/8 photoperiod. Ambient daylight is supplemented with a combination of high pressure sodium and metal halide lamps such that the minimum light intensity 2 m above pot level is 1,500 ft-candles. Greenhouse temperature is maintained within 3° C. of 38° C. during the day and 22° C. at night. The plants are irrigated as needed with a solution containing 400 mg/L of 20-20-20 fertilizer (W. R. Grace & Co., Fogelsville, Pa.) plus 8 mg/L chelated iron (Ciba-Geigy, Greensboro, N.C.).

Approximately 50–60 days after planting, male influorescences (tassels) are shedding pollen and silks have emerged from female influorescences (ears). Pollen is collected by placing a paper bag over the tassel of a plant of the inbred line A188. A female plant of the inbred line B73 is prepared for pollination on the day before pollen availability by cutting off the tip of the husks and silks of an unfertilized ear shoot. The next day, after the silks have grown to form a thick "brush" all the same length, pollen is carefully applied to the silks and the entire ear is covered with a paper bag.

When the developing hybrid embryos reach a length of approximately 1.5–2.0 mm (10–14 days after pollination), the ear is excised and surface sterilized by emersion in 70% v/v ethanol for 10 minutes followed by soaking in 20% v/v commercial bleach (1% sodium hypochlorite) for 30 minutes. Following a sterile, distilled water rinse, immature embryos are aseptically isolated and placed onto a "callus" medium with the embryo axis in contact with the medium (scutellar-side away from the medium). The "callus" medium consists of the following components: N6 basal salts and vitamins (Chu et al., ( 1978) *Proc. Symp. Plant Tissue Cult.*, Science Press, Peking, pp 43–56) 20 g/L sucrose, 691 mg/L proline, 100 mg/L casein hydrolysate, 1 mg/L 2,4-dichloro-phenoxyacetic acid (2,4-D), and 2.5 g/L gelrite (Kelco, Inc., San Diego, Calif.) adjusted to pH 5.8.

The immature, hybrid embryos are incubated at 28° C. in the dark for 10–30 days during which time callus tissue, displaying various types of morphology, proliferates from the scutellar region. The callus tissue produced during this time is classified into three distinct types: i) soft, granular, translucent callus lacking any apparent morphological organization (known as non-embryogenic); ii) compact, nodular, yellowish-to-white callus consisting of groups of somatic embryos (often fused) with distinct scutellar- and coleoptile-like structures (known as Type I); and iii) soft callus with numerous globular and elongated somatic embryos on suspensor-like structures (known as Type II). Type II callus is the most suitable for establishing friable, embryogenic cultures. Sometimes entire scutella will proliferate with this type of tissue or at times only small sectors exhibiting this morphology will develop. At this point, selective sub-culture is necessary whereby only tissue with well-defined globular and elongated somatic embryos along with some subtending undifferentiated, soft tissue is transferred to fresh "callus" medium.

Every 10–14 days, the callus is sub-cultured to fresh "callus" medium being careful to select only tissue of the correct morphology. For the first 8–10 weeks, selection is for Type II callus only, to increase the amount of tissue and to select against non-embryogenic and Type I. At each subculture, less than 100 mg of tissue is typically selected from a callus that has reached a size of 1 g. Thus, the amount of Type II callus will not increase to more than 1 g for the first 8–12 weeks due to the strict selection for tissue type. During the first 3 months, some lines (a line is defined as originating from a single hybrid embryo) will be discarded if they lose their Type II morphology. At about 8–16 weeks in well established Type II cultures, selection of a different type of tissue can proceed. This tissue (known as Type III) is different from Type. II in that it is somewhat more homogeneous in morphology and relatively undifferentiated with no visible somatic embryos. The color will vary from light-to-bright yellow. Normally, it takes about 16–20 weeks to get this homogeneous, Type III tissue in sufficient amounts for routine experimentation (0.5–1.0 g).

During the 14–20 week period of Type III callus establishment, more lines are discarded if they revert to Type II or Type I after repeated selection. At 14–20 weeks of age, the cultures are checked for their ability to regenerate plants (see Example 16, Section C). Lines that do not regenerate are discarded. Cultures capable of maintaining Type III morphology and regenerating plants are referred to as friable, embryogenic callus.

B. Transformation via Microparticle Propulsion

Plasmid DNA is adsorbed onto the surface of gold particles prior to use in transformation experiments. The gold particles are spherical with diameters ranging from about 1.5–3.0 microns in diameter (Aldrich Chemical Co., Milwaukee, Wis.). Adsorption is accomplished by adding 74 µL of 2.5M calcium chloride and 30 µL of 0.1M spermidine to 300 µL of DNA/gold suspension (70 µg pDAB219A, 70 µg pDAB1199, 0.01M Tris buffer, and 1 mM EDTA). The DNA-coated gold particles are vortexed immediately, then allowed to settle to the bottom of an Eppendorf tube and the resultant clear liquid is completely drawn off. The DNA-coated gold particles are then resuspended in 1 mL of 100% ethanol. The suspension is then diluted to 15 mg DNA/gold per mL of ethanol for use in microparticle propulsion experiments.

Approximately 250 mg of friable, embryogenic callus tissue, 5–7 days following sub-culture, is arranged in a thin layer on a 1 cm diameter piece of filter paper (Schleicher and Schuell, Inc., Keene, N.H.) placed on the surface of "callus" medium. The callus tissue is allowed to dry out slightly by allowing the plates to stand uncovered in a laminar flow hood for several minutes before use. In preparation for particle bombardment, the callus is covered with a 104 micron stainless steel screen. The DNA-coated gold particles are accelerated at the friable, embryogenic callus tissue using the particle bombardment apparatus described in European Patent Application EP 0 405 696 A1. Each callus tissue sample is bombarded 10–15 times with each bombardment delivering approximately 1 µL of DNA-coated gold suspension.

III. Selection of Transformed Tissue and Plant Regeneration

After bombarding the sample, callus tissue is allowed to incubate for 1–2 days under the conditions described previously (see Example 16, Section I). After 1–2 days, each tissue sample is divided into approximately 60 equal pieces (1–3 mm diameter) and transferred to fresh "callus" medium containing 30 mg/L Basta. Every three weeks, callus tissue is non-selectively transferred to fresh Basta-containing "callus" medium. At this concentration of herbicide, very little growth is observed. After 8–16 weeks, sectors proliferating from a background of growth inhibited tissue is observed. This tissue is isolated from the other callus and maintained separately on Basta-containing "callus" medium and selectively sub-cultured every 10–14 days. At this point, a histochemical assay for gus expression is performed by placing small samples of callus tissue into 24-well microliter dishes (Corning, New York, N.Y.) containing approximately 500 µL of assay buffer (0.2M sodium phosphate pH 8.0, 0.1 mM each of potassium ferricyanide and potassium ferrocyanide, 1.0M sodium EDTA, and 1 mg/L 5-bromo-4-chloro-3-indolyl-beta-D-glucuronide). Patatin gene expression is also assayed via immunoblot analysis with patatin antiserum.

Basta-resistant, gus- and patatin-positive callus is selectively sub-cultured to "induction" medium and incubated at 28° C. in low light (125 ft-candles) for one week followed by one week in high light (325 ft-candles) provided by cool fluorescent lamps. The "induction" medium is composed of MS salts and vitamins (Murashige and Skoog, 1962), 30 g/L sucrose, 100 mg/L myo-inositol, 5 mg/L benzyl-amino purine, 0.025 mg/L 2,4-D, 2.5 g/L Gelrite adjusted to pH 5.7. Following this two week induction period, the callus is then non-selectively transferred to "regeneration" medium and incubated in high light at 28° C. The "regeneration" medium is composed of MS salts and vitamins, 30 g/L sucrose, and 2.5 g/L gelrite adjusted to pH 5.7. Every 14–21 days the callus is subcultured to fresh "regeneration" medium selecting for tissue which appears to be differentiating leaves and roots. Both "induction" and "regeneration" media contain 30 mg/L Basta. Plantlets are transferred to 10 cm pots containing approximately 1 kg of dry soil mix, moistened thoroughly, and covered with clear plastic cups for approximately 4 days. At the 3-5 leaf-stage, plants are transplanted to larger pots and grown to maturity as previously described (see Example 16, Section A). Self- or sibling-pollinations is performed on plants regenerated from the same culture. Crosses to non-transformed parental lines (i.e., B73 or A188) can also be performed in order to obtain transgenic progeny analysis.

D. Confirmation of Patatin Gene Integration

To confirm the presence of the patatin gene in regenerated plants and progeny, Southern blot analysis of genomic DNA is performed. DNA for each plant is prepared from lyophilized leaf tissue as follows. Approximately 500 mg of tissue is placed into a 16 mL polypropylene tube (Becton Dickenson, Lincoln Park, N.J.) into which is added 9 mL of CTAB extraction buffer (6.57 mL water, 0.9 mL of 1.0M Tris pH7.5, 1.26 mL of 5M sodium chloride, 0.18 mL of 0.5M EDTA, 0.09 g mixed alkyl tri-methyl ammonium bromide, and 0.09 mL beta-mercaptoethanol) and immediately incubated in a 60° C. water bath with occasional mixing. After about 60 minutes, 4.5 mL of 24:1 chloroform/octanol is added and gently mixed for approximately 5 minutes. Following a 10 minute centrifuge at 900×g at room temperature, the top aqueous layer is poured into a 16 mL polypropylene tube containing 6 mL of isopropanol where DNA precipitation occurs.

The precipitated DNA is removed with a glass hook and transferred to a 5 mL disposable tube containing 1-2 mL of 76% ethanol and 0.2M sodium acetate for 20 minutes. The DNA is then rinsed on the hook briefly in a microfuge tube containing 1 mL 76% ethanol and 10 mM ammonium acetate before being transferred to a microfuge tube containing 400 µL of TE buffer (10 mM Tris pH 8.0 and 1 mM EDTA) and placed on a rocker overnight at 4° C. The next day, undissolved solids is removed by centrifugation at high speed for 10 minutes. The DNA-containing supernatant is then pipetted into a new microfuge tube and stored at 4° C.

The concentration of DNA in the sample is determined by measuring absorbance at 260 nm with a spectrophotometer. Approximately 8 µg of DNA is digested with either of the restriction enzymes BamH1 or EcoR1 as suggested by the manufacturer (Bethesda Research Laboratory, Gaithersburg, Md.). This combination of enzymes cuts out the patatin gene intact. The DNA is then fractionated on a 0.8% agarose gel and transferred onto nylon membranes as suggested by the manufacturer (Schleicher and Schuell, Inc., Keene, N.H.). A patatin gene fragment from pDAB1199 is used as a probe.

Probe DNA is prepared by random primer labeling with an Oligo Labeling Kit (Pharmacia LKB Biotechnology, Inc. Piscataway, N.J.) as per the supplier's instructions with 50 microCuries 32-P-dCTP. Blots are then washed at 60° C. in 0.25×SSC (30 mM sodium chloride, 3.0 mM sodium citrate) and 0.2% sodium dodecyl sulfate for 45 minutes, blotted dry, and exposed to XXAR-5 film overnight with two intensifying screens.

To assess resistance to insect attack, transgenic plants expressing the maximal levels of patatin are grown in 12" pots in soil. The soil is infested with *Diabrotica virgifera* eggs and the plants monitored for viability, height, root mass and standability over the course of 4 weeks. Plants expressing patatin are significantly protected from the effects of Diabrotica larval damage. Alternatively, transgenic plants and populations of transgenic plants expressing patatin are assessed for Diabrotica resistance by the methods detailed in "Methods for the Study of Pest Diabrotica" (1986) eds., J. L. Krysan and T. A. Miller, Springer-Verlag, New York, pp 172-180.

Example 17

Transformation of Rice Plants

A gene having the sequence set forth in FIG. 1, encoding patatin, is introduced into rice plants (*Oryza sativa*) using substantially the procedures set forth in Christou, et al. (1991), BIO/TECHNOLOGY, 9:957-962. The gene is inserted into the rice tissue culture using the transformation techniques set forth in Example 16.

Example 18

Transformation of Potato Plants

Figure 12:
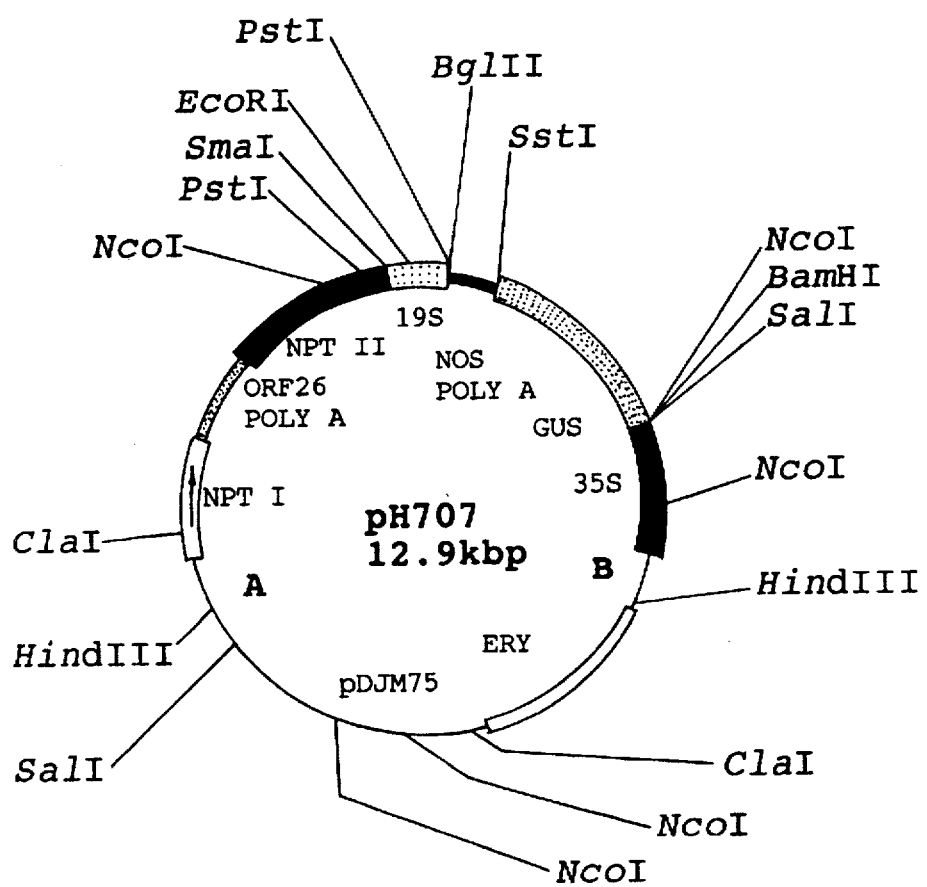
FIG. 12 shows the plasmid map of pH707.

Transformation of potato plants (*Solanum tuberosum* L.) is effected using substantially the same procedures set forth in Shahin and Simpson (1986), *HortScience*, 21(5):1199-1202. The binary vector used for transformation is pH707 (see FIG. 12), is based on the broad host range plasmid RP4. It contains the A and B borders of an octopine-type-Ti plasmid flanking a unique BglI cloning site, the selectable marker 19S-nptII orf 26 and the scorable marker 35S-gus-nos. The tetracycline-resistance gene of RP4 was replaced by erthromycin- and kanamycin-resistance genes for selection in bacteria.

Although the invention has been described in considerable detail, with reference to certain preferred embodiments thereof, it will be understood that variations and modifications can be affected within the spirit and scope of the invention as described above and as defined in the appended claims.

What is claimed is:

1. A method of protecting a plant or a part thereof against insect infestation by one or more corn rootworms, potato beetles, armyworms, borers, cutworms, wireworms, earworms and aphids, comprising presenting to a loci wherein said insect(s) is to be controlled or combated an insect controlling amount of a naturally occurring plant non-specific lipid acyl hydrolase, said plant non-specific lipid acyl hydrolase having an amino acid sequence that includes the serine hydrolase active site motif Gly-Xxx-Ser-Xxx-Gly, said plant non-specific lipid acyl hydrolase being one that is inactivated by treatment with diisopropyl fluorophosphate, and said plant non-specific lipid acyl hydrolase being derived from a plant species other than that of the plant or plant part to be protected.

2. The method of claim 1, wherein the plant non-specific lipid acyl hydrolase is isolated from potato tuber and leaves, leaves of *P. multiflora* or *P. vulgaris*, rice bran, barley endosperm, maize roots or alfalfa.

3. The method of claim 2, wherein the plant non-specific lipid acyl hydrolase is a protein having the amino acid sequence of one of the patatin polypeptides set forth in FIG. 3.

4. The method of claim 1, wherein the plant protected from insect infestation is maize, rice or potato.

5. A method of protecting a plant or a part thereof wherein the plant is not a potato plant, against insect infestation by one or more corn rootworms, potato beetles, armywormsr borers, cutworms, wireworms, earworms and aphids, comprising presenting to a loci wherein said insect(s) is to be controlled or combated an insect controlling amount of a naturally occurring patatin.

* * * * *

SEQUENCE LISTING ( 1 ) GENERAL INFORMATION:

( i i i ) NUMBER OF SEQUENCES: 49

( 2 ) INFORMATION FOR SEQ ID NO:1:

( i ) SEQUENCE CHARACTERISTICS:
( A ) LENGTH: 1380 base pairs
( B ) TYPE: nucleic acid
( C ) STRANDEDNESS: single ( D ) TOPOLOGY: linear ( i i ) MOLECULE TYPE: cDNA ( x i ) SEQUENCE DESCRIPTION: SEQ ID NO:1:

| | | | | | | |
|---|---|---|---|---|---|---|
| ATCTTTTTTA | ATTTTATTTT | TTATGATATT | AGCAACTACT | AGTTCAACAT | GTGCTAAGTT | 60 |
| GGAAGAAATG | GTGACTGTTC | TTAGTATTGA | TGGAGGTGGA | ATTAAGGGAA | TCATTCCAGC | 120 |
| TACCATTCTC | GAATTTCTTG | AAGGACAACT | TCAGGAAGTG | GACAATAATA | AAGATGCAAG | 180 |
| ACTTGCAGAT | TACTTTGATG | TAATTGGAGG | AACAAGTACA | GGAGGTTTAT | TGACTGCTAT | 240 |
| GATAACTACT | CGAAATGAAA | ACAATCGACC | CTTTGCTGCT | GCCAAGATA | TTGTACCCTT | 300 |
| TTACTTCGAA | CATGGCCCTC | ATATTTTAA | TTATAGTGGT | TCAATTATTG | GCCCAATGTA | 360 |
| TGATGGAAAA | TATCTTCTGC | AAGTTCTTCA | AGAAAAACTT | GGAGAAACTC | GTGTGCATCA | 420 |
| AGCTTTGACA | GAAGTTGCCA | TCTCAAGCTT | TGACATCAAA | ACAAATAAGC | CAGTAATATT | 480 |
| CACTAAGTCA | AATTTAGCAA | AGTCTCCAGA | ATTGGATGCT | AAGATGTATG | ACATATGCTA | 540 |
| TTCCACAGCA | GCAGCTCCAA | TATATTTTCC | TCCACATTAC | TTTATTACTC | ATACTAGTAA | 600 |
| TGGTGATATA | TATGAGTTCA | ATCTTGTTGA | TGGTGGTGTT | GCTACTGTTG | GTGATCCGGC | 660 |
| GTTATTATCC | CTTAGCGTTG | CAACGAGACT | TGCACAAGAG | GATCCAGCAT | TTTCTTCAAT | 720 |
| TAAGTCATTG | GATTACAAGC | AAATGTTGTT | GCTCTCATTA | GGCACTGGCA | CTAATTCAGA | 780 |
| GTTTGATAAA | ACATATACAG | CACAAGAGGC | AGCTAAATGG | GGTCCTCTAC | GATGGATGTT | 840 |
| AGCTATACAG | CAAATGACTA | ATGCAGCAAG | TTCTTACATG | ACTGATTATT | ACATTCTAC | 900 |
| TGTTTTTCAA | GCTCGTCATT | CACAAAACAA | TTACCTCAGG | GTTCAAGAAA | ATGCATTAAC | 960 |
| ATGCATTAAC | AGGCACAACT | ACTGAAATGG | ATGATGCGTC | TGAGGCTAAT | ATGGAATTAT | 1020 |
| TAGTACAAGT | TGGTGAAAAA | TTATTGAAGA | AACCAGTTTC | CAAAGACAGT | CCTGAAACCT | 1080 |
| ATGAGGAAGC | TCTAAAGAGG | TTTGCAAAAT | TGCTCTCTGA | TAGAAAGAAA | CTCCGAGCAA | 1140 |
| ACAAATCTTC | TTATTAATTC | AAGGTCTCGG | GTTGTAGTAG | TAACCTTACT | ATGCTAAATA | 1200 |
| ATAAACGCTT | GCAATATTTA | TGATTGCACG | CATTTAAGTA | TTTCAACCTC | AAAATAAAAA | 1260 |
| GGAGTTTGAG | GGATAAATTT | CAATAGAAAT | GTCTCTCTAT | GTAATGTGTG | CTTGGATTAT | 1320 |
| GTAACCTTTT | GGTTGTGTTA | AATATTTAAA | TAAATTATCG | TTAAAAAAAA | AAAAAAAAA | 1380 |

( 2 ) INFORMATION FOR SEQ ID NO:2:

( i ) SEQUENCE CHARACTERISTICS:
( A ) LENGTH: 1339 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:2:

| | | | | | | |
|---|---|---|---|---|---|---|
| CTAAATCTGT | TTTAGTTTTA | ATTTTTATGA | TATTAGCAAC | TACTAGTTCA | ACATTTGCTA | 60 |
| CGTTGGGAGA | AATGGTGACT | GTTCTTAGTA | TTGATGGAGG | TGGAATTAAG | GGAATCATTC | 120 |
| CGGGTATCAT | TCTCGAATTT | CTTGAAGGAC | AACTTCAGAA | AATGGACAAT | AATGCAGATG | 180 |
| CAAGACTTGC | AGATTACTTT | GATGTAATTG | GAGGAACAAG | TACAGGAGGT | TTATTGACTG | 240 |
| CTATGATAAC | TACTCCAAAT | GAAAACAATC | GACCCTTTGC | AGCTGCTAAA | GATATTGTAC | 300 |
| CTTTTTACTT | CCAACATGGC | CCTCATATTT | TAATTCTAG | TACTGGCCAA | TTTTTTGGCC | 360 |
| CAAAATATGA | TGGAAAATAT | CTTATGCAAG | TGCTTCAAGA | AAAACTTGGA | GAAACTCGTG | 420 |
| TGCATCAAGC | TTTGACAGAA | GTTGCCATCT | CAAGCTTTGA | CATCAAAACA | AATAAGCCAG | 480 |

| | | | | | |
|---|---|---|---|---|---|
| TAATATTCAC | CAAGTCAAAT | TTAGCAAAGT | CTCCAGAATT | GGATGCTAAG | ATGTCTGACA | 540
| TATGTTATTC | CACAGCAGCA | GCTCCAACAT | ATTTCCCTCC | ACATTACTTT | GCTACTAATA | 600
| CTAGTAATGG | AGATAAATAT | GAGTTCAATC | TTGTTGATGG | TGCTGTTGCT | ACTGTTGCTG | 660
| ATCCGGCGTT | ATTATCCGTT | AGCGTTGCAA | CGAGACGTGC | AGAAGAGGAT | CCAGCATTTG | 720
| CTTCAATTAG | GTCATTGAAT | TACAAGCAAC | TGTTGTTGCT | CTCATTAGGC | ACTGGCACTA | 780
| ATTCAGAGTT | TGATAAAACA | CATACAGCAC | AAGAGACAGC | TAAATGGGGT | GCTCTACAAT | 840
| GGATGTTGGT | TATACAGCAA | ATGACTGAGG | CAGCAAGTTC | TTACATGACT | GATTATTACC | 900
| TTTCTACTGT | TTTTCAAGAT | CTTCATTCAC | AAAACAATTA | CCTCAGGGTT | CAAGAAAATG | 960
| CATTAACAGG | CACAACTACT | AAAGCGGATG | ATGCTTCTGA | GGCTAATATG | GAATTATTAG | 1020
| TACAAGTTGG | TGAAAATTTA | TTGAAGAAAC | CAGTTTCCAA | AGACAATCCT | GAAACCTATG | 1080
| AGGAAGCTCT | AAAGAGGTTT | GCAAAATTGC | TTTCTGATAG | GAAGAAATTT | CGAGCAAACA | 1140
| AAGCATCTTA | TTAATTCAAG | GTCTCGGGTT | GTAGTTGTAA | ATTTATTATG | CTAAATAATA | 1200
| AGCGCTTGCA | AAGTTCTATG | AGGGATAAAT | TTCATTAGAA | ATGTCTCTCT | ATGTAATGTG | 1260
| TTGGATTATG | TAACCTTTTG | GTTGTGTTTA | ATGTTTAAAT | AAATTATATA | TGGTGAAAAA | 1320
| AAAAAAAAAA | AAAAAAAA | | | | | 1339

(2) INFORMATION FOR SEQ ID NO:3:

(i) SEQUENCE CHARACTERISTICS:
      (A) LENGTH: 381 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:3:

```
Ser Phe Leu Ile Leu Phe Phe Met Ile Leu Ala Thr Thr Ser Ser Thr
  1               5                  10                  15

Cys Ala Lys Leu Glu Glu Met Val Thr Val Leu Ser Ile Asp Gly Gly
             20                  25                  30

Gly Ile Lys Gly Ile Ile Pro Ala Thr Ile Leu Glu Phe Leu Glu Gly
             35                  40                  45

Gln Leu Gln Glu Val Asp Asn Asn Lys Asp Ala Arg Leu Ala Asp Tyr
         50                  55                  60

Phe Asp Val Ile Gly Gly Thr Ser Thr Gly Gly Leu Leu Thr Ala Met
 65                  70                  75                  80

Ile Thr Thr Arg Asn Glu Asn Asn Arg Pro Phe Ala Ala Ala Lys Asp
                 85                  90                  95

Ile Val Pro Phe Tyr Phe Glu His Gly Pro His Ile Phe Asn Tyr Ser
                100                 105                 110

Gly Ser Ile Ile Gly Pro Met Tyr Asp Gly Lys Tyr Leu Leu Gln Val
             115                 120                 125

Leu Gln Glu Lys Leu Gly Glu Thr Arg Val His Gln Ala Leu Thr Glu
        130                 135                 140

Val Ala Ile Ser Ser Phe Asp Ile Lys Thr Asn Lys Pro Val Ile Phe
145                 150                 155                 160

Thr Lys Ser Asn Leu Ala Lys Ser Pro Glu Leu Asp Ala Lys Met Tyr
                165                 170                 175

Asp Ile Cys Tyr Ser Thr Ala Ala Ala Pro Ile Tyr Phe Pro Pro His
            180                 185                 190
```

```
Tyr Phe Ile Thr His Thr Ser Asn Gly Asp Ile Tyr Glu Phe Asn Leu
            195                 200                 205

Val Asp Gly Gly Val Ala Thr Val Gly Asp Pro Ala Leu Leu Ser Leu
    210                 215                 220

Ser Val Ala Thr Arg Leu Ala Gln Glu Asp Pro Ala Phe Ser Ser Ile
225                 230                 235                 240

Lys Ser Leu Asp Tyr Lys Gln Met Leu Leu Leu Ser Leu Gly Thr Gly
                245                 250                 255

Thr Asn Ser Glu Phe Asp Lys Thr Tyr Thr Ala Gln Glu Ala Ala Lys
            260                 265                 270

Trp Gly Pro Leu Arg Trp Met Leu Ala Ile Gln Gln Met Thr Asn Ala
        275                 280                 285

Ala Ser Ser Tyr Met Thr Asp Tyr Tyr Ile Ser Thr Val Phe Gln Ala
    290                 295                 300

Arg His Ser Gln Asn Asn Tyr Leu Arg Val Gln Glu Asn Ala Leu Thr
305                 310                 315                 320

Gly Thr Thr Thr Glu Met Asp Asp Ala Ser Glu Ala Asn Met Glu Leu
                325                 330                 335

Leu Val Gln Val Gly Glu Lys Leu Leu Lys Lys Pro Val Ser Lys Asp
            340                 345                 350

Ser Pro Glu Thr Tyr Glu Glu Ala Leu Lys Arg Phe Ala Lys Leu Leu
        355                 360                 365

Ser Asp Arg Lys Lys Leu Arg Ala Asn Lys Ser Ser Tyr
370                 375                 380
```

( 2 ) INFORMATION FOR SEQ ID NO:4:

( i ) SEQUENCE CHARACTERISTICS:
        ( A ) LENGTH: 383 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Lys Ser Val Leu Val Leu Ile Phe Met Ile Leu Ala Thr Thr Ser Ser
1               5                   10                  15

Thr Phe Ala Thr Leu Gly Glu Met Val Thr Val Leu Ser Ile Asp Gly
            20                  25                  30

Gly Gly Ile Lys Gly Ile Ile Pro Gly Ile Ile Leu Glu Phe Leu Glu
        35                  40                  45

Gly Gln Leu Gln Lys Met Asp Asn Asn Ala Asp Ala Arg Leu Ala Asp
    50                  55                  60

Tyr Phe Asp Val Ile Gly Gly Thr Ser Thr Gly Gly Leu Leu Thr Ala
65                  70                  75                  80

Met Ile Thr Thr Pro Asn Glu Asn Asn Arg Pro Phe Ala Ala Ala Lys
                85                  90                  95

Asp Ile Val Pro Phe Tyr Phe Gln His Gly Pro His Ile Phe Asn Ser
            100                 105                 110

Ser Thr Gly Gln Phe Phe Gly Pro Lys Tyr Asp Gly Lys Tyr Leu Met
        115                 120                 125

Gln Val Leu Gln Glu Lys Leu Gly Glu Thr Arg Val His Gln Ala Leu
    130                 135                 140

Thr Glu Val Ala Ile Ser Ser Phe Asp Ile Lys Thr Asn Lys Pro Val
145                 150                 155                 160

Ile Phe Thr Lys Ser Asn Leu Ala Lys Ser Pro Glu Leu Asp Ala Lys
```

|     |     |     |     | 165 |     |     |     | 170 |     |     |     | 175 |     |     |
|-----|-----|-----|-----|-----|-----|-----|-----|-----|-----|-----|-----|-----|-----|-----|
| Met | Ser | Asp | Ile | Cys | Tyr | Ser | Thr | Ala | Ala | Pro | Thr | Tyr | Phe | Pro |
|     |     |     | 180 |     |     |     | 185 |     |     |     |     | 190 |     |     |
| Pro | His | Tyr | Phe | Ala | Thr | Asn | Thr | Ser | Asn | Gly | Asp | Lys | Tyr | Glu | Phe |
|     |     | 195 |     |     |     |     | 200 |     |     |     |     | 205 |     |     |
| Asn | Leu | Val | Asp | Gly | Ala | Val | Ala | Thr | Val | Ala | Asp | Pro | Ala | Leu | Leu |
|     | 210 |     |     |     |     | 215 |     |     |     |     | 220 |     |     |     |
| Ser | Val | Ser | Val | Ala | Thr | Arg | Arg | Ala | Glu | Glu | Asp | Pro | Ala | Phe | Ala |
| 225 |     |     |     |     | 230 |     |     |     | 235 |     |     |     |     | 240 |
| Ser | Ile | Arg | Ser | Leu | Asn | Tyr | Lys | Gln | Leu | Leu | Leu | Ser | Leu | Gly |
|     |     |     |     | 245 |     |     |     | 250 |     |     |     | 255 |     |     |
| Thr | Gly | Thr | Asn | Ser | Glu | Phe | Asp | Lys | Thr | His | Thr | Ala | Gln | Glu | Thr |
|     |     |     | 260 |     |     |     | 265 |     |     |     |     | 270 |     |     |
| Ala | Lys | Trp | Gly | Ala | Leu | Gln | Trp | Met | Leu | Val | Ile | Gln | Gln | Met | Thr |
|     |     | 275 |     |     |     | 280 |     |     |     |     | 285 |     |     |     |
| Glu | Ala | Ala | Ser | Ser | Tyr | Met | Thr | Asp | Tyr | Tyr | Leu | Ser | Thr | Val | Phe |
|     | 290 |     |     |     |     | 295 |     |     |     | 300 |     |     |     |     |
| Gln | Asp | Leu | His | Ser | Gln | Asn | Asn | Tyr | Leu | Arg | Val | Gln | Glu | Asn | Ala |
| 305 |     |     |     |     | 310 |     |     |     | 315 |     |     |     |     | 320 |
| Leu | Thr | Gly | Thr | Thr | Thr | Lys | Ala | Asp | Asp | Ala | Ser | Glu | Ala | Asn | Met |
|     |     |     | 325 |     |     |     | 330 |     |     |     |     | 335 |     |     |
| Glu | Leu | Leu | Val | Gln | Val | Gly | Glu | Asn | Leu | Leu | Lys | Lys | Pro | Val | Ser |
|     |     |     | 340 |     |     |     | 345 |     |     |     | 350 |     |     |     |
| Lys | Asp | Asn | Pro | Glu | Thr | Tyr | Glu | Glu | Ala | Leu | Lys | Arg | Phe | Ala | Lys |
|     |     | 355 |     |     |     | 360 |     |     |     |     | 365 |     |     |     |
| Leu | Leu | Ser | Asp | Arg | Lys | Lys | Phe | Arg | Ala | Asn | Lys | Ala | Ser | Tyr |
| 370 |     |     |     |     | 375 |     |     |     | 380 |     |     |     |     |     |

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
GGGGACTCTA GAGGATCCCC GGGTGGTCAG TCCCTT                                    36
```

( 2 ) INFORMATION FOR SEQ ID NO:6:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

```
GAATTTCCCC                                                                 10
```

( 2 ) INFORMATION FOR SEQ ID NO:7:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

```
GATCCGGATC CG                                                              12
```

( 2 ) INFORMATION FOR SEQ ID NO:8:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

TCGACGGATC CG         12

( 2 ) INFORMATION FOR SEQ ID NO:9:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

CAGATCTGTG CA         12

( 2 ) INFORMATION FOR SEQ ID NO:10:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

AATTGAGATC TC         12

( 2 ) INFORMATION FOR SEQ ID NO:11:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GGGGACTCTA GAGGATCCCG AATTCCCC         29

( 2 ) INFORMATION FOR SEQ ID NO:12:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GATCGTGATC AC         12

( 2 ) INFORMATION FOR SEQ ID NO:13:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

CAGATCTGCA GATCTGCATG GGCGATG         27

( 2 ) INFORMATION FOR SEQ ID NO:14:

( i ) SEQUENCE CHARACTERISTICS:
    ( A ) LENGTH: 57 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:14:

GATCCAGCTG AAGGCTCGAC AAGGCAGATC CACGGAGGAG CTGATATTTG GTGGACA  57

( 2 ) INFORMATION FOR SEQ ID NO:15:

( i ) SEQUENCE CHARACTERISTICS:
    ( A ) LENGTH: 57 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:15:

AGCTTGTCCA CCAAATATCA GCTCCTCCGT GGATCTGCCT TGTCGAGCCT TCAGCTG  57

( 2 ) INFORMATION FOR SEQ ID NO:16:

( i ) SEQUENCE CHARACTERISTICS:
    ( A ) LENGTH: 64 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:16:

AGCTGTGGAT AGGAGCAACC CTATCCCTAA TATACCAGCA CCACCAAGTC AGGGCAATCC  60

CGGG  64

( 2 ) INFORMATION FOR SEQ ID NO:17:

( i ) SEQUENCE CHARACTERISTICS:
    ( A ) LENGTH: 64 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:17:

TCGACCCGGG ATTGCCCTGA CTTGGTGGTG CTGGTATATT AGGGATAGGG TTGCTCCTAT  60

CCAC  64

( 2 ) INFORMATION FOR SEQ ID NO:18:

( i ) SEQUENCE CHARACTERISTICS:
    ( A ) LENGTH: 62 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:18:

CCGGGCCATT TGTTCCAGGC ACGGGATAAG CATTCAGCCA TGGGATATCA AGCTTGGATC  60

CC  62

( 2 ) INFORMATION FOR SEQ ID NO:19:

( i ) SEQUENCE CHARACTERISTICS:
    ( A ) LENGTH: 62 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:19:

TCGAGGGATC CAAGCTTGAT ATCCCATGGC TGAATGCTTA TCCCGTGCCT GGAACAAATG    60

GC    62

( 2 ) INFORMATION FOR SEQ ID NO:20:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

GATATCAAGC TTGGATCCC    19

( 2 ) INFORMATION FOR SEQ ID NO:21:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

CGGTACCTCG AGTTAAC    17

( 2 ) INFORMATION FOR SEQ ID NO:22:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

CATGGTTAAC TCGAGGTACC GAGCT    25

( 2 ) INFORMATION FOR SEQ ID NO:23:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

ATCTGCATGG GTG    13

( 2 ) INFORMATION FOR SEQ ID NO:24:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

GGGGACTCTA GAGGATCCAG    20

( 2 ) INFORMATION FOR SEQ ID NO:25:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

```
GACGGATCTG                                                                         10
```

( 2 ) INFORMATION FOR SEQ ID NO:26:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

```
GTTAACTCGA GGTACCGAGC TCGAATTTCC CC                                                 32
```

( 2 ) INFORMATION FOR SEQ ID NO:27:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

```
CTCGAGATCT AGATATCGAT GAATTCCC                                                      28
```

( 2 ) INFORMATION FOR SEQ ID NO:28:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

```
TATGGATCCT GTGATAACCG ACATATGCCC CGGTTTCGTT G                                       41
```

( 2 ) INFORMATION FOR SEQ ID NO:29:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

```
TCCTGATCTG TGCAGGTCCC C                                                             21
```

( 2 ) INFORMATION FOR SEQ ID NO:30:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

```
GGGGACTCTA GAGGATCCGG ATCCGTCGAC ATGGTC                                             36
```

( 2 ) INFORMATION FOR SEQ ID NO:31:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

```
GGGGAATTGG AGAGCTCGAA TTTCCCC                                                       27
```

( 2 ) INFORMATION FOR SEQ ID NO:32:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

GGGAATTGAG ATCAGGATCT CGAGCTCGGG                                            30

( 2 ) INFORMATION FOR SEQ ID NO:33:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

GGGAATTCAT CGATATCTAG ATCTCGAGCT CGGGGTACCG AGCTCGAATT C          51

( 2 ) INFORMATION FOR SEQ ID NO:34:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

GGAATGATTC CTTAATTCCA CCTCCATCAA TACT                                    34

( 2 ) INFORMATION FOR SEQ ID NO:35:

( i ) SEQUENCE CHARACTERISTICS:
        ( A ) LENGTH: 88 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

CATGGCAACT ACTAAATCTT TTTTAATTTT ATTTTTATG ATATTAGCAA CTACTAGTTC    60

AACATGTTAA CGGTACCCGG GCCATGGA                                            88

( 2 ) INFORMATION FOR SEQ ID NO:36:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

AGCTTCCATG GCCCGGGTAC CGTTAACATG TTGAACTAGT AGTTGCTAAT ATCAAAAAAT    60

AAAATTAAAA AAGATTTAGT AGTTGC                                                86

( 2 ) INFORMATION FOR SEQ ID NO:37:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:37:

Met Ala Thr Thr Lys Ser Phe Leu Ile Leu Phe Phe Met Ile Leu Ala
1               5                   10                  15

Thr Thr Ser Ser Thr Cys Ala Lys Leu Glu Glu Met Val Thr
            20              25                  30

( 2 ) INFORMATION FOR SEQ ID NO:38:

( i ) SEQUENCE CHARACTERISTICS:
    ( A ) LENGTH: 44 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:38:

GCTCTAGAAC TAGTGGATCC ATGGCGTTGG AAGAAATGGT GCTG                    44

( 2 ) INFORMATION FOR SEQ ID NO:39:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:39:

CTTTTCCCAG TCACGAC                                                  17

( 2 ) INFORMATION FOR SEQ ID NO:40:

( i ) SEQUENCE CHARACTERISTICS:
    ( A ) LENGTH: 24 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:40:

Met Ala Leu Glu Glu Met Val Thr Val Leu Ser Ile Asp Gly Gly Gly
1               5                   10                  15

Ile Lys Gly Ile Ile Pro Ala Thr
            20

( 2 ) INFORMATION FOR SEQ ID NO:41:

( i ) SEQUENCE CHARACTERISTICS:
    ( A ) LENGTH: 23 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:41:

Lys Leu Glu Glu Met Val Thr Val Leu Ser Ile Asp Gly Gly Gly Ile
1               5                   10                  15

Lys Gly Ile Ile Pro Ala Thr
            20

( 2 ) INFORMATION FOR SEQ ID NO:42:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:42:

CATGTGCCAT GG                                                                                    12

( 2 ) INFORMATION FOR SEQ ID NO:43:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

AGCTTCCATG GCA                                                                                   13

( 2 ) INFORMATION FOR SEQ ID NO:44:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:44:

```
Met  Ala  Thr  Thr  Lys  Ser  Phe  Leu  Ile  Leu  Phe  Phe  Met  Ile  Leu  Ala
1                  5                       10                      15

Thr  Thr  Ser  Ser  Thr  Cys  Ala  Met  Ala  Leu  Glu  Glu  Met  Val  Thr
                20                      25                      30
```

( 2 ) INFORMATION FOR SEQ ID NO:45:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:45:

```
Lys  Ser  Val  Leu  Val  Leu  Phe  Phe  Met  Ile  Leu  Ala  Thr  Thr  Ser  Ser
1                  5                       10                      15

Thr  Cys  Ala  Thr  Leu  Gly  Glu  Met  Val  Thr
                20                      25
```

( 2 ) INFORMATION FOR SEQ ID NO:46:

( i ) SEQUENCE CHARACTERISTICS:
        ( A ) LENGTH: 1030 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:46:

```
AAGCTTGCAT  GCCTGCAGAT  CTGCATGGGT  GGAGACTTTT  CAACAAAGGG  TAATATCCGG     60
AAACCTCCTC  GGATTCCATT  GCCCAGCTAT  CTGTCACTTT  ATTGTGAAGA  TAGTGGAAAA    120
GGAAGGTGGC  TCCTACAAAT  GCCATCATTG  CGATAAAGGA  AAGGCCATCG  TTGAAGATGC    180
CTCTGCCGAC  AGTGGTCCCA  AGATGGACC   CCCACCCACG  AGGAGCATCG  TGGAAAAAGA    240
AGACGTTCCA  ACCACGTCTT  CAAAGCAAGT  GGATTGATGT  GATCATCGAT  GGAGACTTTT    300
```

| | | | | | |
|---|---|---|---|---|---|
|CAACAAAGGG|TAATATCCGG|AAACCTCCTC|GGATTCCATT|GCCCAGCTAT|CTGTCACTTT|360|
|ATTGTGAAGA|TAGTGGAAAA|GGAAGGTGGC|TCCTACAAAT|GCCATCATTG|CGATAAAGGA|420|
|AAGGCCATCG|TTGAAGATGC|CTCTGCCGAC|AGTGGTCCCA|AAGATGGACC|CCCACCCACG|480|
|AGGAGCATCG|TGGAAAAGA|AGACGTTCCA|ACCACGTCTT|CAAAGCAAGT|GGATTGATGT|540|
|GATATCTCCA|CTGACGTAAG|GGATGACGCA|CAATCCCACT|ATCCTTCGCA|AGACCCTTCC|600|
|TCTATATAAG|GAAGTTCATT|TCATTTGGAG|AGAACACGGG|GGACTCTAGA|GGATCCAGCT|660|
|GAAGGCTCGA|CAAGGCAGTC|CACGGAGGAG|CTGATATTTG|GTGGACAAGC|TGTGGATAGG|720|
|AGCAACCCTA|TCCCTAATAT|ACCAGCACCA|CCAAGTCAGG|GCAATCCCCA|GATCAAGTGC|780|
|AAAGGTCCGC|CTTGTTTCTC|CTCTGTCTCT|TGATCTGACT|AATCTTGGTT|TATGATTCGT|840|
|TGAGTAATTT|TGGGGAAAGC|TCCTTTGCTG|CTCCACACAT|GTCCATTCGA|ATTTTACCGT|900|
|GTTAGCAAG|GGCGAAAAGT|TTGCATCTTG|ATGATTTAGC|TTGACTATGC|GATTGCTTTC|960|
|CTGGACCCGT|GCAGCTGCGC|TCGGATCTGG|GGCCATTTGT|TCCAGGCACG|GGATAAGCAT|1020|
|TCAGCCATGG| | | | | |1030|

( 2 ) INFORMATION FOR SEQ ID NO:47:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:47:

CAAGCTTGGC TGCAGGTC                                                18

( 2 ) INFORMATION FOR SEQ ID NO:48:

( i ) SEQUENCE CHARACTERISTICS:
( A ) LENGTH: 11 base pairs
( B ) TYPE: nucleic acid
( C ) STRANDEDNESS: single
( D ) TOPOLOGY: linear ( x i ) SEQUENCE DESCRIPTION: SEQ ID NO:48:

CTGTGATAAC C                                                       11

( 2 ) INFORMATION FOR SEQ ID NO:49:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( x i ) SEQUENCE DESCRIPTION: SEQ ID NO:49:

AATTGAGATC TC                                                      12